United States Patent
Chen et al.

(10) Patent No.: US 8,679,534 B2
(45) Date of Patent: *Mar. 25, 2014

(54) HMG-COA REDUCTASE INHIBITOR EXTENDED RELEASE FORMULATION

(75) Inventors: Chih-Ming Chen, Davie, FL (US); Joseph Chou, Coral Springs, FL (US); David Wong, Hollywood, FL (US)

(73) Assignee: Andrx Labs, LLC, Davie, FL (US)

( * ) Notice: Subject to any disclaimer, the term of this patent is extended or adjusted under 35 U.S.C. 154(b) by 835 days.

This patent is subject to a terminal disclaimer.

(21) Appl. No.: 11/355,335

(22) Filed: Feb. 16, 2006

(65) Prior Publication Data

US 2006/0141035 A1 Jun. 29, 2006

Related U.S. Application Data

(63) Continuation of application No. 09/435,576, filed on Nov. 8, 1999, now abandoned, which is a continuation-in-part of application No. 09/339,494, filed on Jun. 24, 1999, now abandoned, which is a continuation of application No. 08/989,253, filed on Dec. 12, 1997, now Pat. No. 5,916,595.

(51) Int. Cl.
| | |
|---|---|
| *A61K 9/28* | (2006.01) |
| *A61K 9/36* | (2006.01) |
| *A61K 9/20* | (2006.01) |
| *A61K 31/35* | (2006.01) |

(52) U.S. Cl.
USPC ........... 424/474; 424/475; 424/479; 424/480; 424/464; 514/460

(58) Field of Classification Search
USPC ......... 424/400, 451, 452, 457, 464, 465, 468, 424/473, 476, 482, 484, 488; 514/460, 960
See application file for complete search history.

(56) References Cited

U.S. PATENT DOCUMENTS

| | | | |
|---|---|---|---|
| 3,671,523 A | 6/1972 | Westphal et al. | |
| 3,691,016 A | 9/1972 | Patel | |
| 3,845,770 A | 11/1974 | Theeuwes et al. | 128/260 |

(Continued)

FOREIGN PATENT DOCUMENTS

| | | |
|---|---|---|
| EP | 0783104 | 7/1997 |
| WO | WO 9005138 | 5/1990 |

(Continued)

OTHER PUBLICATIONS

Hatano, Harumi, et al., Pharmaceutical Preparation Inform of Coated Capsule Releasable at Lower Part Digestive Tract, *Caplus*, 1997:195672.

(Continued)

*Primary Examiner* — Lakshmi Channavajjala
(74) *Attorney, Agent, or Firm* — Florek & Endres PLLC

(57) ABSTRACT

Controlled release oral solid dosage form for the reduction of serum cholesterol levels in humans include a drug comprising an alkyl ester of hydroxy substituted naphthalenes (e.g., lovastatin) and a controlled release carrier, such that the dosage form provides a mean time to maximum plasma concentration ($T_{max}$) of the drug which occurs at about 10 to about 32 hours after oral administration on a once-a-day basis to human patients. The dosage form provides a therapeutically effective reduction in serum cholesterol levels. Methods of reducing serum cholesterol levels in humans are also disclosed.

7 Claims, 10 Drawing Sheets

(56) References Cited

U.S. PATENT DOCUMENTS

| | | | |
|---|---|---|---|
| 3,916,899 A | 11/1975 | Theeuwes et al. | 424/424 |
| 3,969,287 A | 7/1976 | Jaworek et al. | |
| 4,063,064 A | 12/1977 | Saunders et al. | 219/121 L |
| 4,088,864 A | 5/1978 | Theeuwes et al. | 219/121 LM |
| 4,195,128 A | 3/1980 | Hildebrand et al. | |
| 4,229,537 A | 10/1980 | Hodgins et al. | |
| 4,231,938 A | 11/1980 | Monaghan et al. | |
| 4,247,642 A | 1/1981 | Hirohara et al. | |
| 4,330,440 A | 5/1982 | Ayers et al. | |
| 4,346,227 A | 8/1982 | Terahara et al. | |
| 4,444,784 A | 4/1984 | Hoffman et al. | |
| 4,503,030 A | 3/1985 | Edgren et al. | |
| 4,522,625 A * | 6/1985 | Edgren | 424/473 |
| 4,615,698 A | 10/1986 | Guittard et al. | |
| 4,647,576 A | 3/1987 | Hoefle et al. | |
| 4,737,456 A | 4/1988 | Weng et al. | |
| 4,739,073 A | 4/1988 | Kathawala | |
| 4,814,183 A | 3/1989 | Zentner | 424/485 |
| 4,915,954 A | 4/1990 | Ayer et al. | 424/473 |
| 4,946,686 A | 8/1990 | McClelland et al. | 424/473 |
| 4,976,967 A | 12/1990 | McClelland et al. | 424/473 |
| 4,994,273 A | 2/1991 | Zentner et al. | 424/422 |
| 4,997,658 A | 3/1991 | Alberts et al. | 424/473 |
| 5,120,548 A | 6/1992 | McClelland et al. | 424/473 |
| 5,137,873 A | 8/1992 | Yankner | |
| 5,177,080 A | 1/1993 | Angerbauer et al. | |
| 5,211,951 A | 5/1993 | Sparer et al. | 424/426 |
| 5,244,916 A | 9/1993 | Bokoch | 514/460 |
| 5,260,069 A | 11/1993 | Chen | |
| 5,273,760 A | 12/1993 | Oshlack et al. | 424/480 |
| 5,273,995 A | 12/1993 | Roth | |
| 5,286,493 A | 2/1994 | Oshlack et al. | 424/468 |
| 5,300,288 A | 4/1994 | Albright | 424/78.08 |
| 5,324,351 A | 6/1994 | Oshlack et al. | 106/153 |
| 5,350,584 A | 9/1994 | McClelland et al. | 424/501 |
| 5,356,467 A | 10/1994 | Oshlack et al. | 106/153 |
| 5,356,896 A | 10/1994 | Kabadi et al. | |
| 5,366,738 A | 11/1994 | Rork et al. | 424/473 |
| 5,376,383 A | 12/1994 | Alberts et al. | 424/473 |
| 5,419,917 A | 5/1995 | Chen et al. | 429/469 |
| 5,458,887 A | 10/1995 | Chen et al. | 424/464 |
| 5,458,888 A | 10/1995 | Chen | 424/464 |
| 5,468,771 A | 11/1995 | Gagliardi et al. | |
| 5,472,708 A | 12/1995 | Chen | 424/451 |
| 5,472,712 A | 12/1995 | Oshlack et al. | 424/480 |
| 5,506,262 A | 4/1996 | Burk et al. | |
| 5,508,040 A | 4/1996 | Chen | 424/451 |
| 5,518,730 A | 5/1996 | Fuisz | 424/426 |
| 5,532,275 A | 7/1996 | Grumet | 514/567 |
| 5,543,154 A * | 8/1996 | Rork et al. | 424/473 |
| 5,558,879 A | 9/1996 | Chen et al. | |
| 5,567,441 A | 10/1996 | Chen | 424/494 |
| 5,582,838 A | 12/1996 | Rork et al. | 424/472 |
| 5,593,846 A | 1/1997 | Schenk et al. | |
| 5,616,593 A | 4/1997 | Patel et al. | 514/321 |
| 5,654,005 A | 8/1997 | Chen et al. | 424/480 |
| 5,668,134 A | 9/1997 | Klimstra et al. | 514/253.08 |
| 5,728,402 A | 3/1998 | Chen et al. | 424/481 |
| 5,736,159 A | 4/1998 | Chen et al. | 424/480 |
| 5,770,594 A | 6/1998 | Hamanaka et al. | |
| 5,817,789 A | 10/1998 | Heartlein et al. | |
| 5,830,503 A | 11/1998 | Chen | 424/480 |
| 5,834,023 A | 11/1998 | Chen | 424/497 |
| 5,837,379 A * | 11/1998 | Chen et al. | 424/465 |
| 5,874,522 A | 2/1999 | Figuly et al. | 528/422 |
| 5,876,948 A | 3/1999 | Yankner | |
| 5,897,910 A | 4/1999 | Rosenberg et al. | 427/2.14 |
| 5,916,595 A | 6/1999 | Chen et al. | 424/480 |
| 5,952,328 A | 9/1999 | Bihovsky et al. | |
| 5,955,317 A | 9/1999 | Suzuki et al. | |
| 5,955,472 A | 9/1999 | Hays et al. | |
| 5,965,553 A | 10/1999 | Bell et al. | |
| 5,976,817 A | 11/1999 | Davies-Heerema et al. | |
| 5,980,941 A | 11/1999 | Raiden et al. | 424/464 |
| 5,985,936 A | 11/1999 | Novak | |
| 6,001,391 A | 12/1999 | Zeidler et al. | 424/467 |
| 6,080,778 A | 6/2000 | Yankner et al. | |
| 6,172,277 B1 | 1/2001 | Tate et al. | |
| 6,251,852 B1 * | 6/2001 | Gould et al. | 514/2 |
| 6,436,441 B1 | 8/2002 | Sako et al. | 424/488 |
| 6,440,387 B1 | 8/2002 | Yankner et al. | |
| 6,472,421 B1 | 10/2002 | Wolozin | |
| 6,485,748 B1 | 11/2002 | Chen et al. | 424/482 |
| 6,680,341 B1 | 1/2004 | Kerc | |
| 2002/0120003 A1 | 8/2002 | Yankner et al. | |
| 2002/0183379 A1 | 12/2002 | Yankner et al. | |
| 2005/0215620 A1 | 9/2005 | Friedhoff et al. | |

FOREIGN PATENT DOCUMENTS

| | | | |
|---|---|---|---|
| WO | WO 9208483 | 5/1992 | |
| WO | WO 9401772 | 1/1994 | |
| WO | WO 9506470 | 3/1995 | |
| WO | 9619201 | 6/1996 | A61K 9/24 |
| WO | WO 9748391 | 12/1997 | |
| WO | WO 9748701 | 12/1997 | |
| WO | 9811879 | 3/1998 | A61K 9/22 |
| WO | WO 9813488 | 4/1998 | |
| WO | WO 9819169 | 5/1998 | |
| WO | WO 9847518 | 10/1998 | |
| WO | WO 9915159 | 4/1999 | |
| WO | WO 9926657 | 6/1999 | |
| WO | WO 9938498 | 8/1999 | |
| WO | WO 0031548 | 6/2000 | |
| WO | WO 0053173 | 9/2000 | |
| WO | WO 0132161 | 5/2001 | |
| WO | WO 0134123 | 5/2001 | |
| WO | WO 02062824 | 8/2002 | |

OTHER PUBLICATIONS

Cheng, Haiyung, et al., Evaluation of Sustained/Controlled-Release dosage Forms of 3-Hydroxy-3-Methylglutaryl-Coenzyme A (HMG-CoA) Reductase Inhibitors in Dogs and Humans, *Pharmaceutical Research* (1993), 10:1683-1687.

McClelland, Gregory A., et al., Placement of 3-Hydroxy-3-Methylglutaryl-Coenzyme A (HMG-CoA) Reductase Inhibitor Efficacy Through Administration of a Controlled Porosity Osmotic Pump Dosage Form, *Pharmaceutical Research* (1991), 8:873-876.

Illingworth, D. Roger, et al., Comparative Efficacy of Once Versus Twice Daily Mevinolin in the Therapy of Familial Hypercholesterolemia, *Clinical Pharmacology Therapy* (1986), 40:338-343.

Physicians' Desk Reference, MEVECORE® p. 1694-1698 (1998).

Remington's Pharmaceutical Sciences, pp. 857-858 (18th Ed. 1990).

Sabbagh, M.N. et al., β-Amyloid and Treatment Opportunities for Alzheimer's Disease, Alzheimer's Disease Review 3:1-19 (1997).

G. McKhan et al., "Clinical Diagnosis of Alzeheimer's disease", Neurobiology, Jul. 1984, 939-944.

E.R. Frears, D.J., et al., The Role of Cholesterol in the Biosynthesis of β-Amyloid, (1999), NueroReport 10(8) 1699-1705.

P.C. May, Commentary: Amyloid-β Deposits: Can you take them to the bank?, (1997), Alzheimer's Disease Review 2, 15-19.

M. Simons, et al., Cholesterol Depletion Inhibits the Generation of β-Amyloid in Hippocampal Neurons, 1998.

Dovey, et al., Functional Gamma-Secretase Inhibitors Reduce Beta-Amyloid Peptide Levels in Brain, Journal of Neurochemistry, vol. 76, No. 1, pp. 173-181; Abstract XP001147446, 2001.

Goodman & Gilman, The Pharmacological Basis of Therapeutics, 9th Ed. pp. 40-59 (1996).

Iwatsubo, T., Amyloid β Protein in Plasma as a Diagnostic Marker for Alzheimer's Disease, Neurobiology of Aging, vol. 19, No. 2, pp. 161-163 (1998).

Westerman MA, et al., Database Biosis [Online] Biosciences Information Services, Philadelphia, PA, US; 2001, Ibuprofen as a Treatment of Cognitive Decline in the TG2576 mouse model of Alzheimer's Disease, Abstract XP002369757.

(56) References Cited

OTHER PUBLICATIONS

Yang et al., Database Biosis [Online] Biosciences Information Services, Philadelphia, PA, US; 2000, Amyloid Beta Peptide (Abeta) Induced TNF-alpha Release From Alzheimer Microglia is Inhibited by Diclofenac, an Anti-inflamatory Drug, Abstract XP 002369758.
Netland EE et al, Database Embase [Online] Elsevier Science Publishers, Amsterdam, NL; 1998, Idomethacin Reverses the Microglial Response to Amyloid [beta]-protein, Abstract XP 002369459.
Gordon T, et al., Lipoproteins, cardiovascular disease, and death: the Framingham Study. Arch Intern Med. 1981; 14: 1128-1131.
Pedersen TR. et al., The Scandinavian Simvastatin Survival Study Group. Randomized trial of cholesterol lowering in 4444 patients with coronary heart disease: the Scandinavian Simvastatin Survival Study (4S). Lancet. 1994; 344: 1383-89.
Shepherd J, et al. Prevention of coronary heart disease with pravastatin in men with hypercholesterolemia. N Engl J Med. 1995; 333:1301-1307.
Sacks FM, et al. The effect of pravastatin on coronary events after myocardial infarction in patients with average cholesterol levels. N Engl J Med. 1996; 335:1001-1009.
Grundy SM, et al., Expert Panel on Detection, Evaluation, and Treatment of High Blood Cholesterol in Adults. Summary of the Second Report of the National Cholesterol Education Program (NCEP) Expert Panel on Detection, Evaluation, and Treatment of High Blood Cholesterol in Adults (Adult Treatment Panel). JAMA. 1993;269: 3015-3023.
Assmann G, et al., European lipid guidelines: therapeutic recommendations. European Atherosclerosis Society. Am J Cardiol. 1989;63: 53H-55H.
Duggan DE, et al. The physiological disposition of lovastatin. Drug Metab Dispos. 1989; 17: 166-173.
Bilheimer DW, et al., Mevinolin stimulates receptor mediated clearance of low density lipoprotein from plasma in familial hypercholesterolemia heterozygotes. Trans Assoc Am Physicians. 1983; 96: 1-9.
Bradford RH, et al. Expanded Clinical Evaluation of Lovastatin (EXCEL) Study Results. 1. Efficacy in modifying plasma lipoproteins and adverse event profile in 8245 patients with moderate hypercholesterolemia. Arch Intern Med. 1991; 151: 43-49.
Waters D, et al. Effects of monotherapy with an HMG-CoA reductase inhibitor on the progression of coronary atherosclerosis as assessed by serial quantitative arteriography. The Canadian Coronary Atherosclerosis Intervention Trial. Circulation. 1994; 89:959-968.
Brown BG, et al., Regression of coronary artery disease as a result of intensive lipid lowering therapy in men with high levels of apolipoprotein B. N Engl J Med. 1990; 323:1289-1298.
Brown, BG, et al., Types of Change in Coronary Stenosis severity and their relative importance in overall progression and regression of coronary disease. Observation from FATS trial. Familial Arteriosclerosis Treatment Study. Ann N Y Acad Sci. 1995; 748: 407-418.
Furberg, CD, et al., Effect of lovastatin on early carotid arteriosclerosis and cardiovascular events. Asymptomatic Carotid Artery Progression Study (ACAPS) Research Group. Circulation. 1994; 90: 1679-1687.
Downs, JR, et al., Primary Prevention of Acute Coronary Events with lovastatin in men and women with average cholesterol levels (Results of AFCAPS/TexCAPS). JAMA. 1998; 279: 1615-1622.
Krukemyer JJ, et al., Lovastatin: a new cholesterol-lowering agent. Pharmacotherapy. 1987;7: 198-210.
Barr WH., The role of intestinal metabolism in bioavailability. In: Welling PG, et al. Editors. Pharmaceutical Bioequivalence. New York: Marcel Dekker;1991:149-168.
De Waziers I, et al., Cytochrome P 450 isoenzymes, epoxide hydrolase and glutathione transferase in rat and human hepatic and extrahepatic tissues. J Pharmacol Exp Ther. 1990; 253: 387-394.
Pan HY, et al., Comparative pharmacokinetics and pharmacodynamics of pravastatin and lovastatin. J Clin Pharmacol. 1990; 30: 1128-1135.
Pentikainen PJ, et al., Comparative pharmacokinetics of lovastatin, simvastatin and pravastatin in humans. J Clin Pharmacol. 1992; 32: 136-140.
Garnett WR, Interactions with hydroxymethylglutaryl-coenzyme A reductase inhibitors. Am J Health-Syst Pharm. 1995; 52: 1639-1645.
Cheng H, et al. Influence of age and gender on the plasma profiles of 3-hydroxy-3-methylglutaryl-coenzyme A (HMO-CoA) reductase inhibitory activity following multiple doses of lovastatin and simvastatin. Pharm Res.1992; 9: 1629-1633.
Yamazaki M, et al., Na+-independent multi specific anion transporter mediates active transport of pravastatin into rat liver. Am J Physiol. 1993; 264: G36-G44.
Botti RE, et al., Concentrations of pravastatin and lovastatin in cerebrospinal fluid in healthy subjects. Clin Neurapharmacal. 1991; 14:256-261.
Halpin RA, et al., Biotransformation of lovastatin. V. Species differences in in viva metabolite profiles of mouse, rat, dog, and human. Drug Metab Dispas.1993; 21:1003-11.
Wang RW, et al., Biotransformation of lovastatin IV. Identification of cytochrome P450 3A proteins as the major enzymes responsible for the oxidative metabolism of lovastatin in rat and human liver microsomes. Arch Biachem Biaphys. 1991; 290: 355-361.
Transon C, et al., In vitro comparative inhibition profiles of major human drug metabolizing cytochrome P450 isoenzymes (CYP2C9, CYP2D6 and CYP3A4) by HMG-CoA reductase inhibitors. Eur J Clin Pharmacal. 1996; 50: 209-215.
Mckenney LM. Lovastatin: a new cholesterol lowering agent. Clin Pharma. 1988;7:21-36.
Pierno, S, et al., Potential Risk of Myopathy by HMG-CoA Reductase Inhibitors: A Comparison of Pravastatin and Simvastatin Effects on Membrane Electrical Properties of Rat Skeletal Muscle Fibers. JPET, 275:1490-1496 (1995).
Masters, SA, et al., In vitro myotoxicity of the 3-hydroxy-3-methylglutaryl aryl coenzyme A reductase inhibitors, pravastatin, lovastatin, and simvastatin, using neonatal rat skeletal myoctes, Tox. Appl. Pharm., 131:163-174 (1995).
Kivisto KY, et al., Expression of CYP3A4, CYP3A5 and CYP3A7 in human duodenal tissue, Br J Clin Pharmacol 42:3 387-9 (1996).
Paine, MF, et al., Characterization of interintestinal and intraintestinal variations in human CYP3 A dependent Metabolism, Phamacol Exp Ther. 283:3 1552-62 (1997).
Kaminsky LS. Small intestinal cytochromes P450. Cult. Rev Toxicol 21:6 407-22 (1991).
Lown KS, et al., Interpatient heterogeneity in expression of CYP3A4 and CYP3A5 in small bowel. Lack of prediction by the erythromycin breath test. Drug Metab Dispos 22:6 947-55; (1994)[published erratum appears in Drug Metab Dispos 23 (3) following table of contents (1995).
Thummel KE, et at., Oral first pass elimination of midazolam involves both gastrointestinal and hepatic CYP3A-rnedlated metabolism, Clin Pharmacol Ther 59:5 491-502 (1996).
Kaminski M, [Systemic localization of mixed function oxidases], Folia Med Cracov 1990 31:3 97-120.
McKinnon RA, et al., Function and localization of cytochromes P450 involved in the metabolic activation of food-derived heterocylic amines, Princess Takamatsu Symp 23:145-53 (1995).
Peters WH. et al., Biotransformation enzymes in human intestine: critical low levels in the colon. Gut 32:4 408-12 (1991).
Lampen A. et al., Drug interactions and inter individual variability of ciclosporin metabolism in the small intestine. Pharmacology 52:3 159-68 (1996).
Rosenberg DW, et al., Dietary modulation of cytochrome P450 in the small intestinal epithelium, Pharmacology 43:1 36-46 (1991).
Hakkak R. et al., Effects of enteral nutrition and ethanol on cytochrome P450 distribution in small intestine of male rats. Gastroenterology 104:6 1611-8 (1993).
Lown KS, Grapefruit juice increases felodipine oral availability in humans by decreasing intestinal CYP3A protein expression, J Clin Invest 99:10 2545-53 (1997).
Wortelboer HM, et al., Effects of cooked brussels sprouts on cytochrome P-450 profile and phase II enzymes in liver and small intestinal mucosa of the rat. Food Chem Toxicol., 1992.
Barr, WH, The role of intestinal metabolism on bioavailability In: Welling PG. et al., editors. Pharmaceutical Bioequivalence. New York: Marcel Dekker, 149-68 (1991).

* cited by examiner

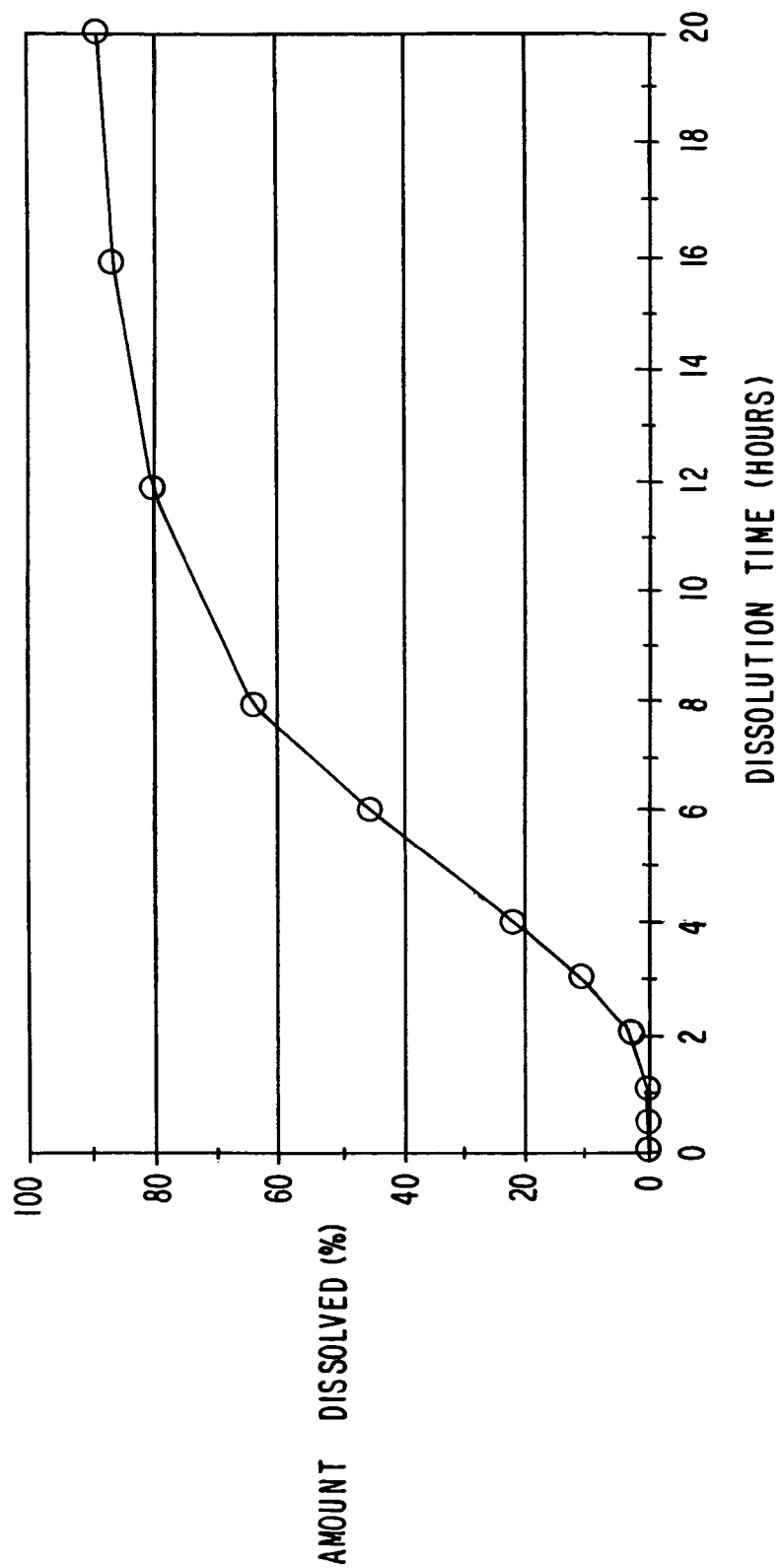

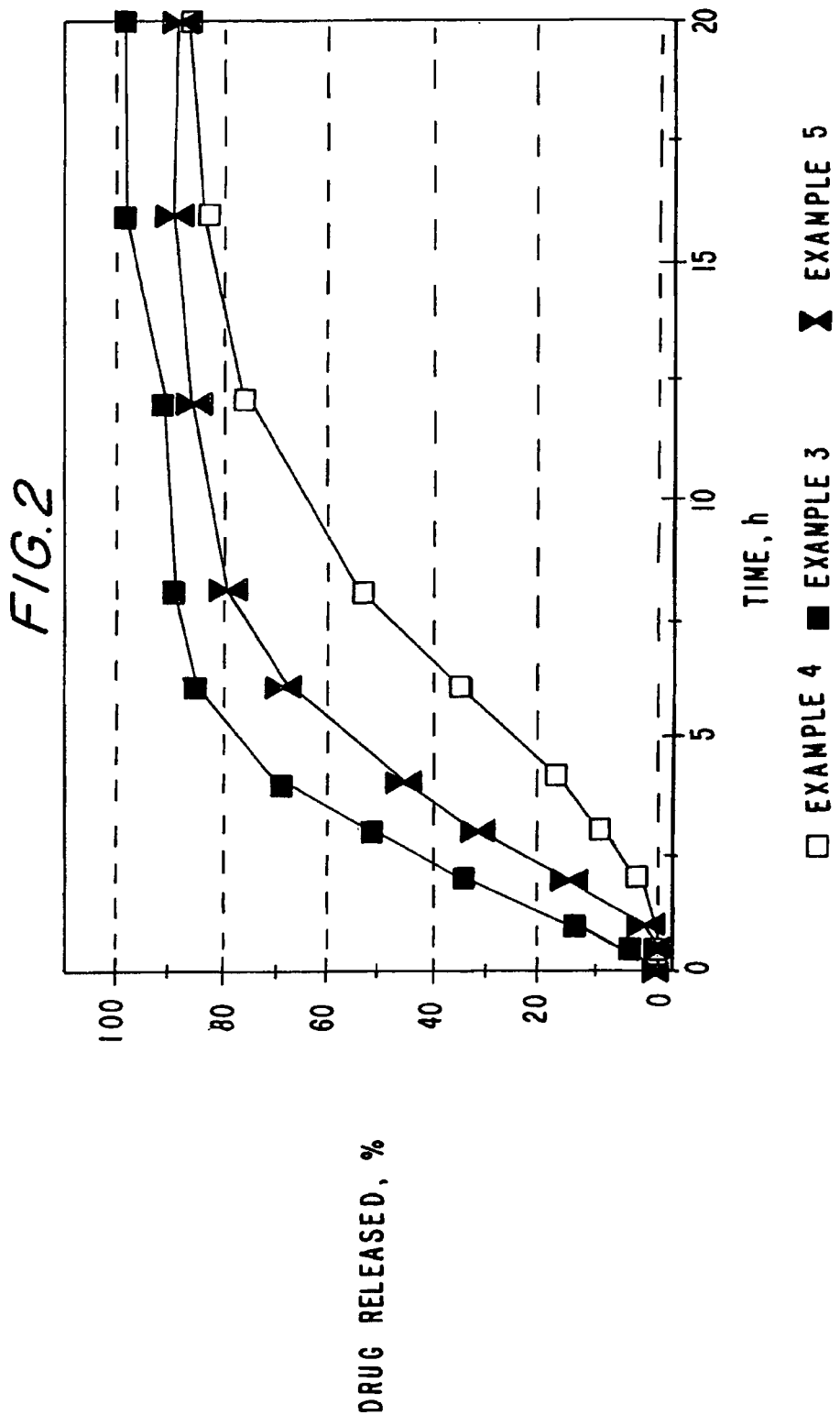

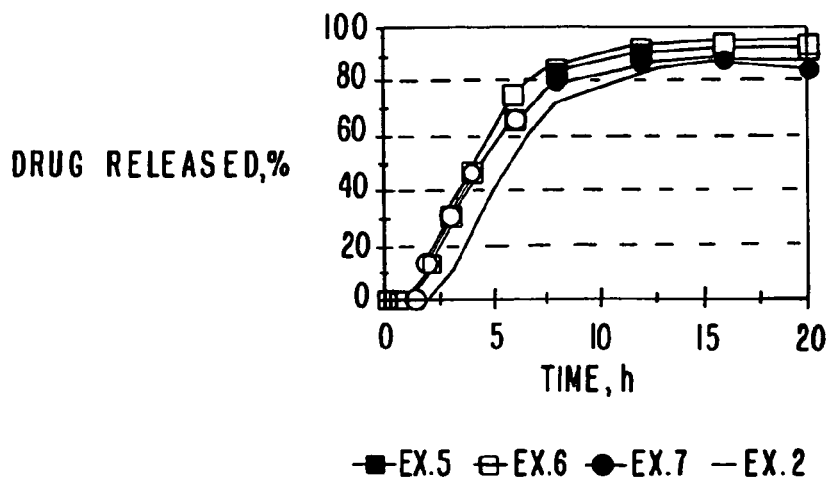
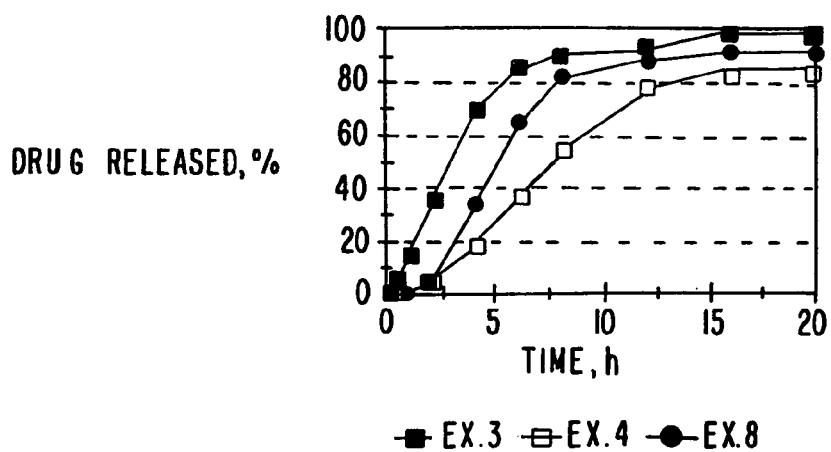
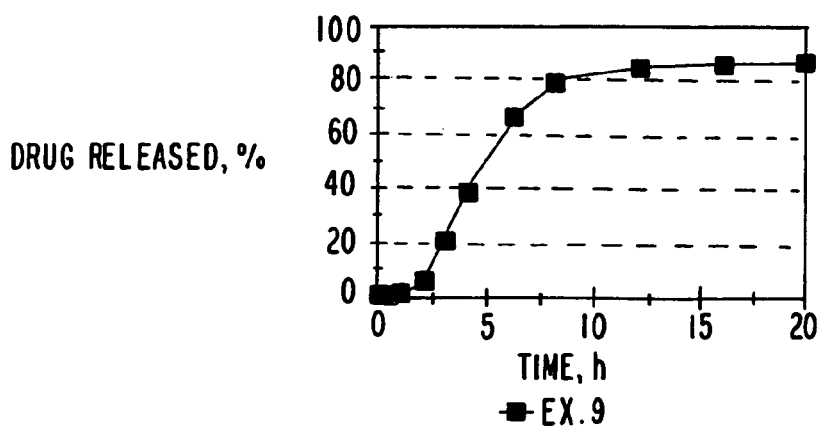

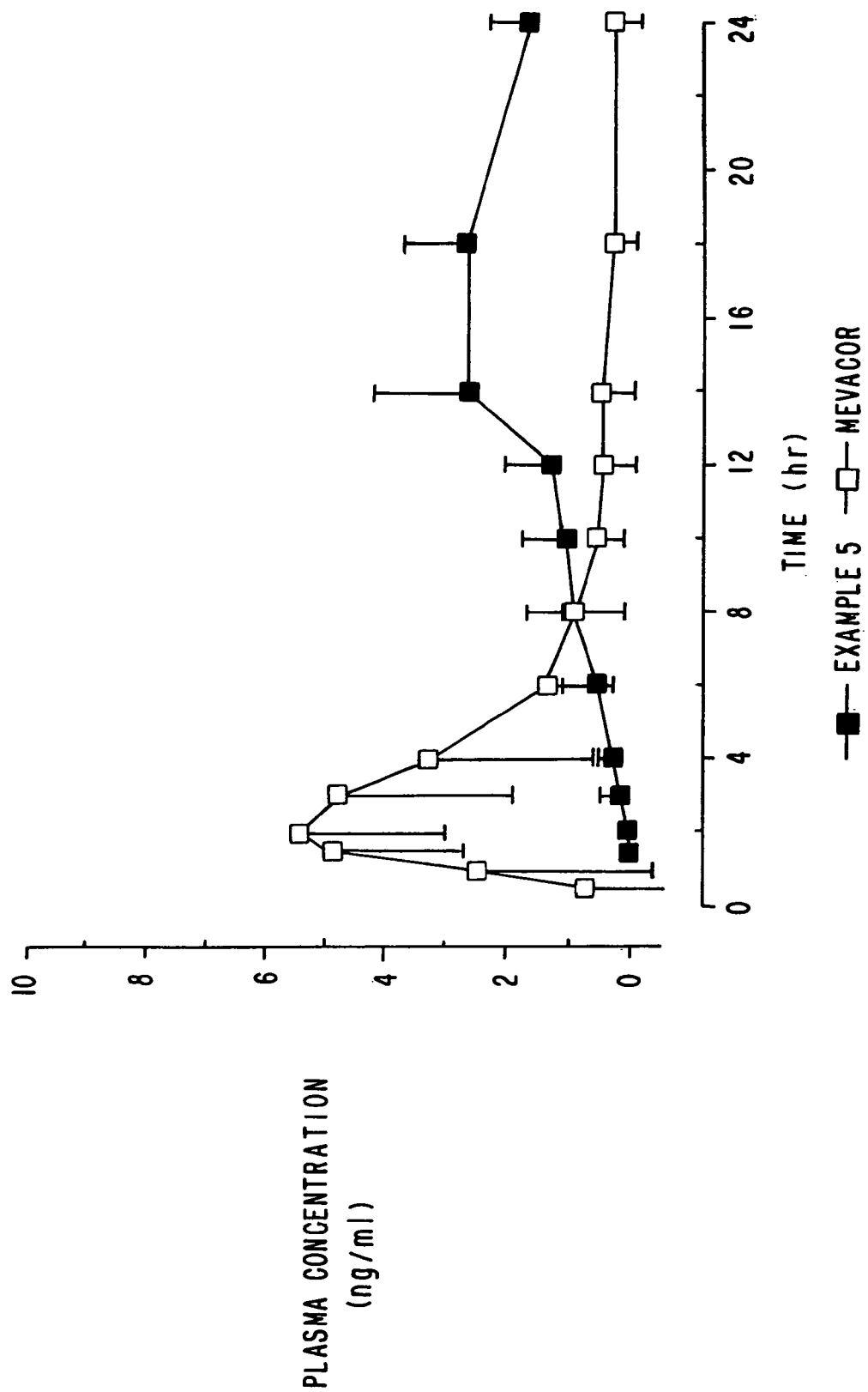

HMG-COA REDUCTASE INHIBITOR EXTENDED RELEASE FORMULATION

CROSS-REFERENCE TO RELATED APPLICATIONS

This application is a continuation of U.S. Ser. No. 09/435,576, filed Nov. 8, 1999 which is a continuation-in-part of U.S. Ser. No. 09/339,494, filed Jun. 24, 1999, which is a continuation of U.S. Pat. No. 5,916,595, filed Dec. 12, 1997.

BACKGROUND OF THE INVENTION

The use of HMG-COA reductase inhibitors for the reduction of serum cholesterol levels is well known. These compounds include alkyl esters of hydroxy substituted naphthalenes which are orally effective in the reduction of serum cholesterol levels. Examples of these compounds include mevastatin which is described in U.S. Pat. No. 3,671,523; lovastatin which is described in U.S. Pat. No. 4,231,938; pravastatin which is described in U.S. Pat. No. 4,346,227; and simvastatin which is described in U.S. Pat. No. 4,444,784. All of these patents are incorporated by reference.

Lovastatin is a metabolite which is produced by the natural fermentation of an fungus of the *Aspergillus* genus. Lovastatin acts systemically to lower blood serum cholesterol levels by disrupting the biosynthesis of cholesterol in the liver, where 70% to 80% of body cholesterol is produced. Specifically lovastatin interrupts a step in the endogenous production of cholesterol by inhibiting the HMG coenzyme A reductase from combining with bile acids in the digestive tract such that the bile acids are excreted from the body without reabsorption. With synthesis in the liver thusly inhibited, the liver cells must take cholesterol from the bloodstream, and they do so by increasing their production of cell surface receptors for LDL cholesterol. Lovastatin formulations are generally capable of lowering the blood serum cholesterol level by about 30-40%. The other compounds of this class are derived from natural or synthetic sources using well known procedures and have similar mechanisms of activity.

However, it is desirable to enhance the activity of these compounds to achieve even greater reductions of blood serum cholesterol levels in connection with the treatment of hypercholesterolemia and other maladies. Accordingly, the present invention provides a novel controlled release formulation of a compound which is an alkyl ester of a hydroxy substituted naphthalene derivative which provides for a gradual release of the compound. This formulation has been prepared to provide a slow controlled release of these compounds in order to provide a more constant level of bioavailability in order to provide an enhanced effect that cannot be achieved by conventional immediate release dosing. The use of a controlled release form of is believed to be specially useful for those who have meals at irregular times or those who frequently eat snacks between meals. These subjects include night shift workers, airline personnel and travelers, and those individuals with blood sugar problems who eat frequent small meals. In addition, it is believed that the human body synthesizes high amounts of cholesterol during the hours of sleep and it is desirable in certain cases to provide therapeutic level of these compounds during periods of sleep.

Controlled release formulations have been described in U.S. Pat. No. 4,615,698 which have been based on an osmotic dosage form which is designed to collapse and cause the faced surfaces to come into a close contacting arrangement as the drug is delivered through a passageway in the semi-permeable wall of the dosage form. In addition, U.S. Pat. No. 4,503,030 discloses an osmotic dosage form which has a passageway and a semi-permeable membrane consisting of a particular cellulose polymer and a pH-sensitive material which could be an enteric coating material. This patent describes the use of 1:1 mixtures of a pH sensitive material and cellulose polymer which are applied at a level of about 70% by weight based on the total weight of the osmotic core tablet and coating material.

In the parent application, the applicants have discovered that a ratio of 0.75:1, and lower, of pH sensitive material to cellulose polymer may be used to provide a stable membrane around an osmotic core tablet at a coating level of 1-4% by weight based on the total weight of the osmotic core tablet and coating material. These osmotic tablets will substantially, completely deliver the compound without the need to provide a passageway in the tablet according to the teachings of the prior art. In addition the osmotic tablet of the invention will provide higher bioavailability and lower peak plasma drug concentrations than are provided by the same weight of the alkyl ester of a hydroxy substituted naphthalene derivative in a conventional immediate release dosage form.

SUMMARY OF THE INVENTION

It is an object of the present invention to provide oral compositions which enhance the activity of antilipemic agents, specifically HMG-CoA reductase inhibitors, to achieve even greater reductions of blood serum cholesterol levels in connection with the treatment of hypercholesterolemia and other maladies.

It is an object of the present invention to provide a controlled release form of an alkyl ester of a hydroxy substituted naphthalene derivative.

It is an object of the present invention to provide a controlled release form of an alkyl ester of a hydroxy substituted naphthalene derivative which provides effective yet novel plasma concentration profiles of the drug.

It is a further object of the present invention to provide methods of treating human patients who have high serum cholesterol levels.

It is a further object of the present invention to provide methods of enhancing the activity of antilipemic agents, specifically HMG-CoA reductase inhibitors, to achieve even greater reductions of blood serum cholesterol levels in connection with the treatment of hypercholesterolemia and other maladies.

It is also an object of the present invention to provide a controlled release dosage formulation of an alkyl ester of a hydroxy substituted naphthalene derivative which substantially completely releases said alkyl ester in about 4 to 30 hours in vitro in a Type 2 USP 23 dissolution apparatus in 2% sodium lauryl sulfate, pH buffer to 7.0 at 37° C. and 50 rpm.

In accordance with the above-mentioned objects and others, the present invention provides a novel controlled release formulation of a compound which is an alkyl ester of a hydroxy substituted naphthalene derivative which provides for a gradual release of the compound. This formulation has been prepared to provide a slow controlled release of these compounds in order to provide a more constant level of bioavailability in order to provide an enhanced effect that cannot be achieved by conventional immediate release dosing.

In view of the above objects and others, the invention is in part directed to a controlled release oral solid dosage form for the reduction of serum cholesterol levels in humans comprising a drug comprising an alkyl ester of hydroxy substituted naphthalenes (e.g., lovastatin) and a controlled release carrier in an amount effective to provide a controlled release of the drug, the dosage form providing a mean time to maximum plasma concentration ($T_{max}$) of the drug which occurs at about 10 to about 32 hours after oral administration to human patients, the dosage form providing a reduction in serum cholesterol levels when administered to human patients on a once-a-day basis.

The invention is further directed to a controlled release oral solid dosage form for the reduction of serum cholesterol levels in humans, comprising a drug comprising an alkyl ester of hydroxy substituted naphthalenes, and a controlled release carrier for the drug, the dosage form providing a substantially complete release of the drug in about 4 to 30 hours in vitro in a Type 2 USP 23 dissolution apparatus in 2% sodium lauryl sulfate, pH buffer to 7.0 at 37° C. and 50 rpm, the dosage form providing a mean time to maximum plasma concentration ($T_{max}$) which occurs at about 10 to about 32 hours after oral administration to human patients, the dosage form achieving a reduction in serum cholesterol levels when administered to human patients on a once-a-day basis.

Further embodiments of the invention relate to a controlled release oral solid dosage form for the reduction of serum cholesterol levels in humans, comprising a drug comprising an alkyl ester of hydroxy substituted naphthalenes, and a controlled release carrier for the drug, the controlled release dosage form providing a dissolution of from about 0% to about 25% drug released after 2 hours; from about 40% to about 85% drug released after 6 hours; and not less than about 75% drug released after 16 hours, when measured in vitro in a Type 2 USP 23 dissolution apparatus in 2% sodium lauryl sulfate, pH buffer to 7.0 at 37° C. and 50 rpm, and which preferably provides a time to maximum plasma concentration ($T_{max}$) of the drug which occurs at about 10 to about 32 hours after oral administration to human patients, the dosage form achieving a reduction in serum cholesterol levels when administered to human patients on a once-a-day basis.

In certain preferred embodiments, the controlled release dosage form provides a dissolution of from about 0% to about 20% drug released after 2 hours; from about 50% to about 80% drug released after 6 hours; and not less than about 80% drug released after 16 hours, when measured in vitro in a Type 2 USP 23 dissolution apparatus in 2% sodium lauryl sulfate, pH buffer to 7.0 at 37° C. and 50 rpm. In certain further preferred embodiments, the controlled release dosage form provides a dissolution of from about 10% to about 15% drug released after 2 hours; from about 65% to about 75% drug released after 6 hours; and not less than about 79% drug released after 16 hours, when measured in vitro in a Type 2 USP 23 dissolution apparatus in 2% sodium lauryl sulfate, pH buffer to 7.0 at 37° C. and 50 rpm.

In certain embodiments, the mean time to maximum plasma concentration of the drug preferably occurs at about 14 to about 24 hours after oral administration.

In certain preferred embodiments of the invention, the mean time to maximum plasma concentration of total HMG-CoA Reductase Inhibitors preferably occurs at about 13 to about 21 hours after oral administration. Preferably, the controlled release formulations of the invention provide a mean time to maximum plasma concentration of active HMG-CoA Reductase Inhibitors which preferably occurs at about 6.2 to about 20.1 hours, and more preferably from about 9.5 to about 15.2 hours after oral administration. Preferably, the controlled release formulations in accordance with the invention provide a mean maximum plasma concentration ($C_{max}$) of total HMG-CoA Reductase Inhibitors from about 4.7 ng/ml to about 25.4 ng/ml, preferably from about 10.5 ng/ml to about 17.3 ng/ml, and a mean maximum plasma concentration ($C_{max}$) of active HMG-CoA Reductase Inhibitors preferably from about 2.1 ng/ml to about 22.5 ng/ml, preferably 6.4 ng/ml to about 13.4 ng/ml (e.g., based on a 40 mg dose of lovastatin).

In certain preferred embodiments of the invention, the drug is selected from the group consisting of lovastatin, a derivative of lovastatin, an active metabolite of lovastatin, mevastatin, pravastatin, sinvastatin, and mixtures thereof.

In certain preferred embodiments of the invention, the controlled release oral solid dosage form includes lovastatin in an amount of from about 10 to about 80 mg (e.g., 10, 20, 40 or 80 mg). In embodiments in which the drug is lovastatin, the formulations preferably provide a maximum plasma concentration ($C_{max}$) of lovastatin from about 1 ng/ml to about 8 ng/ml, preferably from about 1.5 ng/ml to about 7.1 ng/ml, and more preferably from about 3 ng/ml to about 4 ng/ml, based on a 40 mg dose of lovastatin (the plasma levels of lovastatin preferably being dose proportional, as described herein in the appended Examples). When the drug is lovastatin, the controlled release formulations of the invention preferably provide a mean $AUC_{0-48hr}$ of lovastatin from about 15 to about 90 ng·hr/ml, more preferably from about 34 to about 77 ng·hr/ml. In certain preferred embodiments of the invention where the drug is lovastatin, the dosage form preferably provides a mean time to maximum plasma concentration of lovastatin acid at about 5.3 to about 28.7 hours after oral administration, and more preferably at about 13.0 to about 20.9 hours, after oral administration. In further preferred embodiments where the drug is lovastatin, the dosage form provides a mean maximum plasma concentration ($C_{max}$) of lovastatin acid from about 1.05 ng/ml to about 7.22 ng/ml, preferably from about 2.50 ng/ml to about 4.90 ng/ml, based on a 40 mg dose of lovastatin. In such embodiments, the dosage from may provide a mean $AUC_{0-48hr}$ of lovastatin acid from about 9.96 to about 132.54 ng·hr/ml, preferably from about 47.5 to about 91.2 ng·hr/ml.

The present invention further relates to a method for reducing serum cholesterol levels in humans, comprising orally administering a drug comprising an alkyl ester of hydroxy substituted naphthalenes in a controlled release oral solid dosage form which provides a mean time to maximum plasma concentration ($T_{max}$) of the drug which occurs at about 10 to about 32 hours after oral administration of said dosage form to human patients, and which achieves an effective reduction in serum cholesterol levels when administered to human patients on a once-a-day basis. In certain preferred embodiments where the drug is lovastatin, it is preferred that after administration the dosage form provides a mean maximum plasma concentration ($C_{max}$) of lovastatin from about 1.5 ng/ml to about 7.1 ng/ml, based on a 40 mg dose of lovastatin (e.g., where the plasma levels and $C_{max}$ of lovastatin is dose proportional), after administration of a single dose to human patients. In certain preferred embodiments, orally administering lovastatin in a controlled release oral solid dosage form provides a mean time to maximum plasma concentration ($T_{max}$) which occurs at about 14 to about 24 hours after oral administration of said dosage form to human patients, and a maximum plasma concentration ($C_{max}$) of the drug of from about 3 ng/ml to about 4 ng/ml (based on a 40 mg dose of lovastatin), such that the dosage form achieves a reduction in serum cholesterol levels when administered to human patients on a once-a-day basis.

The present invention further relates to a method for reducing serum cholesterol levels in humans, comprising orally administering a drug comprising an alkyl ester of hydroxy substituted naphthalenes in a controlled release oral solid dosage form to human patients in the morning (e.g., after administration of a single dose of lovastatin), which dosage form provides a mean time to maximum plasma concentration ($T_{max}$) at about 11 to about 32 hours after oral administration to human patients, the dosage form achieving a reduction in serum cholesterol levels when administered to human patients on a once-a-day basis. In this embodiment, when the drug is lovastatin, the dosage form preferably provides a mean maximum plasma concentration ($C_{max}$) of said drug from about 1.5 ng/ml to about 6.9 ng/ml, based on a 40 mg dose of lovastatin. In this embodiment, where the human patients are administered the dosage form after breakfast in the fed state, it is preferred that the dosage form provides a mean time to maximum plasma concentration ($T_{max}$) which occurs at about 16 to about 32 hours after oral administration of a single dose, more preferably at about 22 to about 26 hours after oral administration, and that it further preferably provides a mean maximum plasma concentration ($C_{max}$) of the drug from about 1.5 ng/ml to about 4.5 ng/ml based on a 40 mg dose of lovastatin, after oral administration of a single dose. When the human patients are adminstered the dosage form in the morning in the fasted state, it is preferred that the dosage form provides a mean time to maximum plasma concentration ($T_{max}$) which occurs at about 5.3 to about 17 hours after oral administration of a single dose, more preferably at about 9 to about 13 hours after oral administration, and preferably provides a mean maximum plasma concentration ($C_{max}$) of the drug from about 2.9 ng/ml to about 6.9 ng/ml, based on a 40 mg dose of lovastatin, after oral administration of a single dose.

The present invention further relates to a method for reducing serum cholesterol levels in humans, comprising orally administering a drug comprising an alkyl ester of hydroxy substituted naphthalenes in a controlled release oral solid dosage form to human patients at dinner time, which dosage form provides a mean time to maximum plasma concentration ($T_{max}$) at about 10.4 to about 20.6 hours after oral administration (e.g., after a single dose), the dosage form achieving a reduction in serum cholesterol levels when administered to human patients on a once-a-day basis. Preferably, where the drug is lovastatin, the dosage form provides a mean maximum plasma concentration ($C_{max}$) of said drug from about 1.9 ng/ml to about 4.4 ng/ml, based on a 40 mg dose of lovastatin. In such embodiments, it is preferred that the mean time to maximum plasma concentration ($T_{max}$) is at about 13.5 to about 17.5 hours after oral administration, and more preferably at about 15.5 hours after oral administration. It is further preferred the dosage form provides a mean maximum plasma concentration ($C_{max}$) of said drug of about 3 ng/ml, based on a 40 mg dose of lovastatin.

The present invention further relates to a method for reducing serum cholesterol levels in humans, comprising orally administering a drug comprising an alkyl ester of hydroxy substituted naphthalenes in a controlled release oral solid dosage form to human patients at bedtime, which dosage form provides a mean time to maximum plasma concentration ($T_{max}$) which occurs at about 10 to about 23.2 hours after oral administration (e.g., of a single dose) to a population of human patients, the dosage form achieving a reduction in serum cholesterol levels when administered to human patients on a once-a-day basis. Preferably, where the drug is lovastatin, the dosage form provides a mean maximum plasma concentration ($C_{max}$) of said drug from about 1 ng/ml to about 8 ng/ml, based on a 40 mg dose of lovastatin. In this embodiment, where the human patients are administered the dosage form at bedtime, it is preferred that the dosage form provides a mean time to maximum plasma concentration ($T_{max}$) which occurs at about 14.2 to about 16.9 hours after oral administration of a single dose, and preferably provides a mean maximum plasma concentration ($C_{max}$) of the drug of about 4 ng/ml, based on a 40 mg dose of lovastatin, after oral administration of a single dose. When administered at bedtime, the dosage forms of the invention preferably provide a mean time to maximum plasma concentration ($T_{max}$) which occurs at about 10 to about 22 hours after oral administration to human patients at steady-state, preferably at about 12 to about 16 hours, and more preferably at about 14 hours after oral administration. Preferably, the dosage form provides a mean maximum plasma concentration ($C_{max}$) of said drug from about 3 ng/ml to about 8 ng/ml, more preferably about 5.5 ng/ml, based on a 40 mg dose of lovastatin at steady-state.

The invention also relates to a method for improving the dose-response relationship achieved via the administration of a statin drug orally administered in immediate release form, comprising orally administering the statin in a controlled release dosage form which provides a mean time to maximum plasma concentration ($T_{max}$) of the statin drug which occurs at about 10 to about 32 hours after oral administration to human patients.

In certain preferred embodiments of the present invention, administration of the controlled release oral solid dosage forms of the invention achieves an accumulation of lovastatin and its latent and active metabolites at steady-state conditions of about 1.4 to about 2 fold the levels attained by immediate release lovastatin administered once daily. In certain preferred embodiments, the dosage forms of the invention provide increased systemic bioavailability of lovastatin, but at the same time do not provide increased bioavailability of lovastatin acid, active or total inhibitors.

The invention is further related to a controlled release oral solid dosage form, comprising a therapeutically effective amount of lovastatin, and a controlled release carrier providing delivery of said lovastatin when said dosage form is orally administered to human patients, such that a mean maximum plasma concentration ($C_{max}$) of lovastatin from about 1 ng/ml to about 5.5 ng/ml and preferably from about 3 ng/ml to about 5.5 ng/ml is attained, after administration of a single dose or at steady-state in a population of human patients in need of such therapy, per 40 mg dose of lovastatin.

The invention is further related to a method for reducing serum cholesterol levels in humans, comprising orally administering a controlled release oral solid dosage form containing a therapeutically effective amount of lovastatin which provides a mean maximum plasma concentration ($C_{max}$) of lovastatin from about 1 ng/ml to about 5.5 ng/ml, preferably from about 3 ng/ml to about 5.5 ng/ml, after administration of a single dose or at steady-state in a population of human patients in need of such therapy, per 40 mg dose of lovastatin.

The invention is further related to a method for providing increased systemic bioavailability of lovastatin, while at the same time not increasing the bioavailability of lovastatin acid, active or total inhibitors compared to an immediate release reference standard form of lovastatin, comprising preparing a controlled release oral solid dosage form of lovastatin which comprises a therapeutically effective amount of lovastatin and a sufficient amount of a controlled release carrier such that the controlled release dosage form provides a dissolution of from about 0% to about 25% lovastatin released after 2 hours; from about 40% to about 85% lovastatin released after 6 hours; and not less than about 75% lovastatin released after 16 hours, when measured in vitro in a Type 2 USP 23 dissolution apparatus in 2% sodium lauryl sulfate, pH buffer to 7.0 at 37° C. and 50 rpm, and such that the dosage form provides a mean time to maximum plasma concentration ($T_{max}$) of lovastatin from about 10 to about 32 hours after oral administration to human patients. The dosage form is administered to human patients on a once-a-day basis.

For purposes of this disclosure, the term "statin" encompasses alkyl esters of hydroxy substituted naphthalenes which are orally effective in the reduction of serum cholesterol levels, and includes but is not limited to examples of these compounds described in U.S. Pat. No. 3,671,523 (include mevastatin); compounds described in U.S. Pat. No. 4,231,938 (including lovastatin); compounds described in U.S. Pat. No. 4,346,227 (including pravastatin); and compounds is described in U.S. Pat. No. 4,444,784 (including simvastatin).

The term "steady state" means that the blood plasma concentration curve for a given drug has been substantially repeated from dose to dose of the drug formulation. The term "single dose" means that the human patient has received a single dose of the drug formulation and the drug plasma concentration has not achieved steady state. The term "multiple dose" means that the human patient has received at least two doses of the drug formulation in accordance with the dosing interval for that formulation (e.g, on a once a day basis). Patients who have received multiple doses of the controlled release formulations of the invention may but not necessarily have attained steady state drug plasma levels, as the term multiple dose is defined herein.

The term "morning" as it is used herein with respect to the dosing of the controlled release formulations of the invention means that the controlled release formulation is orally administered early in the day after the patient has awakened from overnight sleep, generally between about 6 a.m. and 11 a.m. (regardless of whether breakfast is eaten at that time, unless so specified herein). The term "dinnertime" as it is used herein with respect to the dosing of the controlled release formulations of the invention means that the controlled release formulation is orally administered at a time when dinner is normally eaten (regardless of whether a meal is actually eaten at that time, unless so specified herein), generally between about 4 p.m. and 8 p.m. The term "bedtime" as it is used herein with respect to the dosing of the controlled release formulations of the invention means that the controlled release formulation is orally administered before the patient goes to bed in the evening, generally between about 8 p.m. and 12 p.m.

The phrase "therapeutically effective reduction" when used herein is meant to signify that serum cholesterol levels are reduced by approximately the same amount as an immediate release reference standard (e.g., Mevacor®) or more, when the controlled release dosage form is orally administered to a human patient on a once-a-day basis.

BRIEF DESCRIPTION OF THE DRAWINGS

FIG. 1 is a graph of in vitro dissolution data which shows the dissolution profile of the formulation of Example 1 in 2% sodium lauryl sulfate at pH 7.0 in $NaH_2PO_4$ buffer in a USP XXII Type II dissolution apparatus at 50 rpm at 37° C.

FIG. 2 is a graph of in vitro dissolution data which shows the dissolution profiles of the formulations of Examples 3, 4 and 5 in 2% sodium lauryl sulfate at pH 7.0 in $NaH_2PO_4$ buffer in a USP XXII Type II dissolution apparatus at 50 rpm at 37° C.

FIG. 3 is a graph of the in-vitro dissolution data which shows the dissolution profiles of Examples 2 and 5-7 under similar conditions as set forth above with respect to FIG. 2.

FIG. 4 is a graph of the in-vitro dissolution data which shows the dissolution profiles of Examples 8 under similar conditions as set forth above with respect to FIG. 3.

FIG. 5 is a graph of the in-vitro dissolution data which shows the dissolution profiles of Examples 9 under similar conditions as set forth above with respect to FIG. 3.

FIG. 6 is a graph of comparative data which shows mean (±SD) plasma concentration time profiles of lovastatin in healthy subjects (n=8) following a single oral dose of a conventional immediate release dose of 40 mg of lovastatin and an extended release 40 mg dose of lovastatin according to the invention (Example 5).

DETAILED DESCRIPTION OF THE INVENTION

Figure 7:
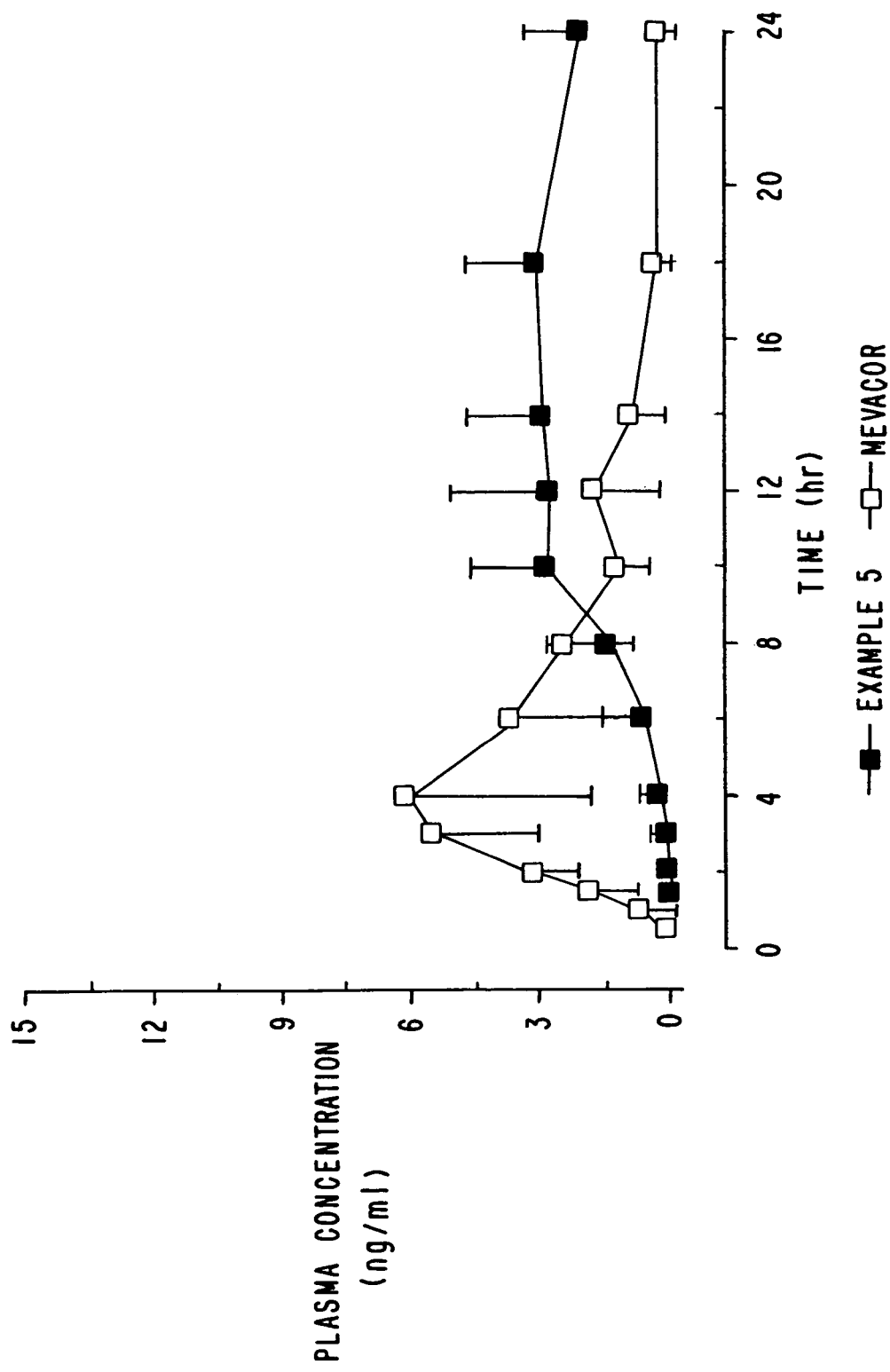
FIG. 7 is a graph of comparative data which shows mean (±SD) plasma concentration time profiles of lovastatin acid in healthy subjects (n=8) following a single oral dose of a conventional immediate release dose of 40 mg of lovastatin and an extended release 40 mg dose of lovastatin according to the invention (Example 5).

The controlled release dosage form is preferably prepared by combining mevastatin, pravastatin, simvastatin or lovastatin with a pharmaceutically acceptable, water swellable polymer and an osmotic agent into a compressed tablet core having an optional first coating for sealing and protection and a second coating comprising a pH sensitive agent water insoluble polymer. Mevastatin, pravastatin, simvastatin and lovastatin are well known compounds that are described in the prior art including the particular patents which have been cited herein. It is also within the scope of the invention to use mixtures of different alkyl esters of hydroxy substituted naphthalenes.

Specifically, a pharmaceutically acceptable, water swellable polymer and an osmotic agent are combined with the drug which may be micronized or unmicronized or amorphous or crystalline and compressed to form the tablet core. The osmotic agent is any nontoxic pharmaceutically acceptable water soluble compound which will dissolve sufficiently in water and increase the osmotic pressure inside the core of the tablet. The osmotic agents include the simple sugars and salts such as sodium chloride, potassium chloride, magnesium sulfate, magnesium sulfate, magnesium chloride, sodium sulfate, lithium sulfate, urea, inositol, sucrose, lactose, glucose, sorbitol, fructose, mannitol, dextrose, magnesium succinate, potassium acid phosphate and the like. The preferred osmotic agent for the tablet core is a simple sugar such as anhydrous lactose in the range of 0-50% by weight, based on the weight of the compressed, uncoated tablet.

The pharmaceutically acceptable, water swellable polymer may be any pharmaceutically acceptable polymer which swells and expands in the presence of water to slowly release the lovastatin. These polymers include polyethylene oxide, methylcellulose, hydroxypropylcellulose, hydroxypropylmethylcellulose and the like. In a preferred embodiment, the water swellable polymer will be polyethylene oxide (obtained from Union Carbide Corporation under the trade name Polyox WSR Coagulant or Polyox WSR N 80) These materials form a viscous gel in water or other solvent system at a sufficient concentration to control the release of the lovastatin. This will generally require a concentration of the pharmaceutically acceptable, water swellable polymer of about 0-50% by weight of the compressed, uncoated tablet.

Binder may be employed in a sufficient amount so that when it is combined with a suitable solvent, mixed with the water soluble osmotic agent and agitated, granules will be formed which may be compressed into a tablet core. Prior to compressing the granules, the conventional solid pharmaceutical diluents such as microcrystalline cellulose, lactose, dextrose and the like may be added to the granule forming mixture in amounts from about 0 to 51% weight based on the weight of the compressed, uncoated tablet. In the present case, the above mentioned osmotic agent, lactose, may function as a binder in the tablet compression step.

In the preparation of the tablets of the invention, various solvents may be used to prepare the granules. In addition, various other diluents, excipients, lubricants, dyes, pigments, dispersants, emulsifiers, etc. may be used to optimize the formulations of the invention.

Additionally, a surfactant is used in the preferred embodiment. The surfactant may be any ionic or non-ionic water soluble surfactant which may be employed in the range of 0-50% by weight or preferably 1-5% by weight. The preferred surfactant for the present formulation is sodium lauryl sulfate but other surfactants such as polysorbate 20, 60 or 80; polyoxl stearate and the like.

Furthermore, the preferred embodiment may comprise a lubricant. Ideally, the lubricant will be in the range of 0.5 to 2.5% by weight of the compressed, uncoated tablet.

After the above described tablet core is formed, it is coated with: 1) an optional protective first coating on the tablet core and/or an optional pH sensitive coating; 2) an outer coating comprising a pH sensitive agent and a water insoluble polymer.

Specifically, a protective first coating may be used at a level in the range of 0-10% by weight which may be applied from a coating system such as opadry Clear sold by Colorcon Corporation. In an especially preferred embodiment, the Opadry Clear will be 2.83% by weight and will be combined with an osmotic agent in the range of 0-10% by weight. While the osmotic agent may be any salt, low molecular weight molecule or water soluble polymers, the preferred agent is sodium chloride. The osmotic agent is added to the coating system when the coating system is being dispersed into purified water. The coating system which contains the osmotic agent may then be sprayed onto the tablets to form a protective coating layer. As mentioned above, this protective first coating is optional.

An optional inner or over coat over the outer coat may also be applied which comprises a pH sensitive polymer which functions as an enteric polymer in that it does not begin to dissolve until pH conditions in excess of the stomach region are encountered. Generally, the pH sensitive materials do not dissolve and begin to release the active drug until a pH above 3.0 and preferably above 5.5. Materials such as such as Eudragit L (copolymer of poly(methacrylic acid, methylmethacrylate), 1:1 ratio; MW (No. Av. 135,000 USP Type A) or Eudragit S (copolymer of poly(methacrylic acid, methylmethacrylate, 1:2 ratio MW (No. Av. 135,000-USP Type B) hydroxypropyl methyl cellulose phthalate, cellulose acetate phthalate, polyvinyl acetate phthalate and the like may be used in the range of 0-30% by weight and preferably 2 to 4 percent by weight of the combined weight of the compressed, uncoated tablet and the inner coating of the pH sensitive polymer.

The outer coating comprises a pH sensitive polymer which functions as an enteric polymer in that it does not begin to dissolve until pH conditions in excess of the pH of the stomach region are encountered and a water insoluble polymer which provide controlled release properties to the coating formulation. The pH sensitive polymer is the same type of material that is described above as the optional inner coating layer. The water insoluble polymer may be a cellulosic polymer such as ethylcellulose, cellulose acylate, cellulose mono-, di- or triacetate. The pH sensitive polymer and the insoluble cellulosic polymer are used at a weight ratio of about 0.1:1 to 0.75:1, preferably 0.25:1 to 0.5:1 of pH sensitive polymer to water insoluble cellulosic polymer. A combined coating weight of about 0.5-5% by weight and preferably 1 to 4% by weight and especially preferred is 1 to 3% by weight of the gained weight based on the weight of the coated tablet core. Cellulose acetate is the preferred water insoluble polymer and the outer coating is preferably applied as a suspension in acetone.

Furthermore, a plasticizer or combination of plasticizers may be added to the inner, outer or over coating to provide elasticity and shape to the coating. while the plasticizer or combination of plasticizers may be any water soluble or water insoluble formulation in the range of 0-10% by weight and preferably 0.5 to 5% by weight of the outer coating composition. Acetyltributyl citrate is the preferred plasticizer but materials such as acetyl triethyl citrate, dibutyl phthalate, triacetin, diethyl phthalate, polyethylene glycol, propylene glycol and the like may be utilized.

An antioxidant such as BHA or BHT may be added to the tablet core as a stabilizer at a level of 0.001 to 0.01% by weight of the tablet core.

Lastly, a channelling agent is mixed with the aforementioned components of the outer coating. A channelling agent may be employed to increase the porosity of the film coating in order-to increase the amount of the fluids that penetrate the tablet core and increase the rate of hydration. This allows the release of the lovastatin after the outer film coat ruptures. Generally, channelling agents may be any salts, surfactants, or short-chain water soluble polymers in a water channel forming effective amount i.e. 1 to 5% by weight, based on the total weight of the core and all coating components. The channeling agents include any pharmaceutically acceptable water soluble salt, surfactant, or short chain water soluble polymer such as sodium chloride, potassium chloride, sucrose, polysorbate-80, hydroxypropyl cellulose, hydroxyethyl cellulose and the like.

Also, the preferred embodiment of the inner or over coating is supplied with an anti-sticking agent such as talc to overcome any tablet to tablet stickiness during the coating process. The amount of anti-sticking agent is an amount which prevents sticking which may be in the range of 0-6% by weight based on the weight of the tablets and the coating materials on a dry weight basis.

Although the applicants do not wish to be bound by any theory by which the invention operates, it is believed that the tablets of the invention release the lovastatin by osmotic pressure. Water is drawn into the tablet and it expands to the point where the outer coating fails in one particular area to form a constricted opening which releases the internal contents of the tablet which contain the drug. Thereafter, the aqueous medium of the tablet shell will continue to release the drug as it dissolves until the osmotic pressure inside the tablet shell equals that of the surrounding environment. At the late stages of the in vivo release of lovastatin, it is believed that the tablet shell will collapse and/or disintegrate completely to substantially completely release the remaining drug. The water insoluble coating is not absorbed in the gastrointestinal tract and is eliminated in the feces.

The tablets of the invention may be made in a smooth faced tablet die. Thereafter the tablet is provided with the outer coating which, because of surface tension, will result in a thinner coating layer over the corners of the tablet which will provide an area in the outer coating which will form a channel to is allow intestinal fluid to reach the core of the tablet.

In certain preferred embodiments, the tablets of the invention will have the following general formula:

TABLE 1

| INGREDIENTS | POSSIBLE RANGE, wt % |
|---|---|
| Tablet Core | |
| Alkyl ester of a substituted naphthalene | 3-20 |
| Water Swellable Polymer | 10-40 |
| Antioxidant | 0.001-0.01 |
| Osmotic Agents | 20-80 |
| Surfactant | 0-5 |
| Lubricant | 0-5 |
| Coatings: | |
| Seal Coating | 0-10 |
| Osmotic Agents | 0-10 |
| Inner Coating | |
| Enteric Polymer | 0-30 |
| Anti-sticking Agent | 0-6 |
| Plasticizer | 0-6 |
| Channelling Agents | 0-6 |
| Outer Coating | |
| Blend of Enteric Polymer and Water-insoluble Polymer | 0.5-5 |
| Plasticizer(s) | 0-1 |
| Channelling Agents | 0.2.5 |
| Overcoat | |
| Enteric Polymer | 0-30 |
| Anti-sticking Agent | 0-6 |
| Plasticizer | 0-6 |
| Channelling Agents | 0-6 |
| TOTAL | 100 |

Other controlled release technologies known to those skilled in the art can be used in order to achieve the controlled release formulations of the present invention, i.e., formulations which provide a mean Tmax of the drug (i.e., a HMG-CoA reductase inhibitor) at the desired time after oral administration, e.g., in general, at about 10 to about 32 hours after oral administration to a population of human patients, and which preferably provide other pharmacokinetic parameters described herein when orally administered to human patients. Such formulations can be manufactured as a controlled oral formulation in a suitable tablet or multiparticulate formulation known to those skilled in the art. In either case, the controlled release dosage form may optionally include a controlled release carrier which is incorporated into a matrix along with the drug (e.g., HMG-COA reductase inhibitors), or which is applied as a controlled release coating.

An oral dosage form according to the invention may be provided as, for example, granules, spheroids, beads, pellets (hereinafter collectively referred to as "multiparticulates") and/or particles. An amount of the multiparticulates which is effective to provide the desired dose of opioid over time may be placed in a capsule or may be incorporated in any other suitable oral solid form. In one preferred embodiment of the present invention, the controlled release dosage form comprises such particles containing or comprising the active ingredient, wherein the particles have diameter from about 0.1 mm to about 2.5 mm, preferably from about 0.5 mm to about 2 mm.

Examples of suitable multiparticulate formulations are those in which the particles comprise inert beads which are coated with the drug. Thereafter, a coating comprising the controlled release carrier is applied onto the beads. Alternatively, a spheronizing agent, together with the drug can be spheronized to form spheroids. Microcrystalline cellulose is preferred. A suitable microcrystalline cellulose is, for example, the material sold as Avicel PH 101 Trade Mark, FMC Corporation). In such embodiments, in addition to drug and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose.

In certain embodiments, the particles comprise normal release matrixes containing the drug. These particles are then coated with the controlled release carrier.

The controlled release coatings useful in the formulations of the present invention should be capable of producing a strong, continuous film that is smooth and elegant, capable of supporting pigments and other coating additives, non-toxic, inert, and tack-free. In one embodiment, coatings are provided to permit either pH-dependent or pH-independent release, e.g., when exposed to gastrointestinal fluid. A pH-dependent coating serves to release the opioid in desired areas of the gastro-intestinal (GI) tract, e.g., the stomach or small intestine, such that an absorption profile is provided which is capable of providing at least about twelve hour and preferably up to twenty-four hour analgesia to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, and the like.

In certain preferred embodiments, the tablet core or multiparticulates containing the drug are coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Such formulations are described, e.g., in detail in U.S. Pat. Nos. 5,273,760 and 5,286,493, hereby incorporated by reference. Other examples of sustained release formulations and coatings which may be used in accordance with the present invention include U.S. Pat. Nos. 5,324,351; 5,356,467, and 5,472,712, hereby incorporated by reference in their entirety. The sustained release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

In other embodiments of the present invention, the desired controlled release of the formulation is achieved via a matrix (either normal or controlled release) having a controlled release coating as set forth above.

The present invention may also utilize a controlled release matrix that affords in-vitro dissolution rates of the drug within the preferred ranges and that releases the drug in a pH-dependent or pH-independent manner. The materials suitable for inclusion in a controlled release matrix will depend on the method used to form the matrix. The controlled release material which may be included in a matrix in addition to the drug includes hydrophilic and/or hydrophobic materials, such as gums, alkycelluloses, cellulose ethers, acrylic resins, and protein derived materials. This list is not meant to be exclusive, and any pharmaceutically acceptable hydrophobic material or hydrophilic material which is capable of imparting controlled release of the active agent may be used in accordance with the present invention.

The hydrophobic material is preferably selected from the group consisting of alkylcelluloses, cellulose ethers, acrylic and methacrylic acid polymers and copolymers, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl metharylates, cynaoethyl methacrylate, aminoalkyl methacrylate copolymer, poly(acrylic acid), poly(methacrylic acid), methacrylic acid alkyamine copolymer, poly(methyl methacrylate), poly(methacrylic acid)(anhydride), polymethacrylate, polyacrylamide, poly(methacrylic acid anhydride), and glycidyl methacrylate copolymers. In other embodiments, the hydrophobic material is selected from materials such as ethylcellulose.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxyalkylcelluloses (such as hydroxypropylcellulose) are preferred. Additionally (or alternatively) the spheroids may contain a water insoluble polymer, especially an acrylic polymer, an acrylic copolymer, such as a methacrylic acid-ethyl acrylate copolymer, or ethyl cellulose.

In addition to the above ingredients, a controlled release matrix may also contain suitable quantities of other materials, e.g. diluents, lubricants, binders, granulating aids, colorants, flavorants and glidants that are conventional in the pharmaceutical art. The quantities of these additional materials will be sufficient to provide the desired effect to the desired formulation. Specific examples of pharmaceutically acceptable carriers and excipients that may be used to formulate oral dosage forms are described in the *Handbook of Pharmaceutical Excipients*, American Pharmaceutical Association (1986), incorporated by reference herein.

If necessary to achieve the desired plasma curve (e.g., Tmax), a portion of the drug may be included in the formulations of the invention in immediate release form. For example, the drug may be included in separate normal release matrix particles, or may be co-administered in a different immediate release composition which is either enveloped within a gelatin capsule or is administered separately. In other embodiments, the particles comprise inert beads which are coated with the drug. Thereafter, a coating comprising the controlled release carrier is applied onto the beads, and then an immediate release drug layer is applied on top of the controlled release coating as an overcoat. Alternatively, in controlled release tablet formulations in which the controlled release carrier is included in a matrix with the drug or the controlled release carrier is applied in a coating on the surface of the tablet, a portion of the drug may be applied on the surface of the tablet as an immediate release drug layer (as an overcoat if the tablet has a controlled release coating).

Further specific controlled release technologies which may be used in conjunction with the present invention include the Assignee's U.S. Pat. Nos. 5,837,379; 5,34,023; 5,830,503; 5,736,159; 5,728,402; 5,654,005; 5,567,441; 5,558,879; 5,532,275; 5,508,040; 5,472,708; 5,458,888; 5,458,887; and 5,419,917, all of which are hereby incorporated by reference.

DESCRIPTION OF THE PREFERRED EMBODIMENTS

The following examples illustrate various aspects of the present invention. They are not to be construed to limit the claims in any manner whatsoever.

Example 1

A tablet having the following formula was prepared:

| | | | |
|---|---|---|---|
| lovastatin | 11.99 | wt % | 40.0 mg |
| Polyox WSR Coagulant, NF* | 4.50 | wt % | 15.0 mg |
| Polyox WSR N 80, NF** | 17.98 | wt % | 60.0 mg |
| lactose (anhydrous) | 50.65 | wt % | 169.0 mg |
| sodium lauryl sulfate | 3.00 | wt % | 10.0 mg |
| silicon dioxide Fumed USP/NF | 0.45 | wt % | 1.5 mg |
| Myvaplex 600P*** | 1.80 | wt % | 6.0 mg |
| Seal Coating: | | | |
| Opadry Clear**** | 2.81 | wt % | 9.4 mg |
| sodium chloride | 0.93 | wt % | 3.1 mg |

-continued

| Inner Coating: | | |
|---|---|---|
| hydroxypropylmethylcell. phthal.55 | 2.27 wt % | 7.58 mg |
| talc | 0.78 wt % | 2.6 mg |
| acetyl tributyl citrate | 0.22 wt % | 0.75 mg |
| sugar, confectioners 6X micronized | 0.62 wt % | 2.08 mg |
| Outer Coating: | | |
| cellulose acetate | 1.00 wt % | 3.32 mg |
| Eudragit S 100₁ | 0.34 wt % | 1.13 mg |
| Triacetin | 0.08 wt % | 0.27 mg |
| polyethylene glycol 400 | 0.08 wt % | 0.27 mg |
| sugar, confectioners 6X micronized | 0.50 wt % | 1.66 mg |
| | 100.0 wt % | 333.66 mg |

*polyethylene oxide Mw No av 5,000,000
**polyethylene oxide Mw No av 200,000
***glyceryl monostearate
****mixture containing hydroxypropyl methyl cellulose and polyethylene glycol
₁Eudragit S 100 (poly(methacrylic acid, methylmethacrylate, 1:2 ratio MW (No. Av. 135,000 - USP Type B)

The following describes the process of making the above described dosage form:
Step 1, the Tablet Core
(a) Granulation
1. Pass Polyox WSR N80, sodium lauryl sulfate and anhydrous lactose through a 30 mesh stainless steel screen.
2. Charge the screened materials and lovastatin (micronized) into a vertical granulator.
3. Dissolve butylated hydroxy anisole in ethanol.
4. Mix ethanol, and purified water.
5. Pre-mix the powder mixture for 5 minutes.
6. Blend the powder mixture again, add the butylated hydroxyanisole solution and then the ethanol/water mixture.
7. Dry the granules at 45-50° C. until the moisture content is lower than 1.8 wt %.
8. Pass the granules through a 1575 mesh using a Comil.
Tabletting
1. Mix Cab-O-Sil and Polyox WSR N80.
2. Pass the mixture of Cab-o-Sil and Polyox WSR N80 through a 24 mesh stainless steel screen with the Polyox WSR Coagulant.
3. Blend the screen materials with lovastatin granules for 15 minutes.
4. Pass Myvaplex through a 30 mesh stainless steel screen and combine with the other screen materials.
5. Blend for five minutes.
6. Compress the blend into tablets (300 mg, round, standard concave, 11/32") which contain 40 mg of lovastatin.
Seal Coating: Opadry Clear
1. Dissolve sodium chloride in purified water.
2. Disperse Opadry Clear into the sodium chloride solution.
3. Spray lovastatin tablets with the aqueous coating suspension using a coater.
Inner Coating: Hydroxypropyl Methylcellulose Phthalate 55
1. Dissolve hydroxypropyl methylcellulose phthalate 55 in acetone using a homogenizer.
2. Add acetyl tributyl citrate to the acetone solution and mix it with a homogenizer until a homogenized dispersion is obtained.
3. Add talc and sugar to the solution and mix it with a homogenizer until a homogenized dispersion is obtained.
4. Replace the homogenizer with a magnetic mixer and stir the coating mixture throughout the coating process.
5. Spray the Opadry Clear coated lovastatin tablets with the coating dispersion in a coater.

Outer Coating: Cellulose Acetate
1. Dissolve cellulose acetate and Eudragit S100 in acetone using a homogenizer.
2. Add polyethylene glycol 400, triactein and sugar to the solution and mix until a homogeneous dispersion is obtained.
3. Spray the coating suspension onto the tablets in a coater.

Release in the above described manner will result in the dissolution profile shown in FIG. 1, which is a graph of in vitro dissolution data which shows the dissolution profile of the formulation of Example 1 in 2% sodium lauryl sulfate at pH 7.0 in $NaH_2PO_4$ buffer in a USP XXII Type II dissolution apparatus at 50 rpm at 37° C.

It is believed that administration of the above described micronized Lovastatin in these amounts will be particularly effective in inhibiting the biosynthesis of cholesterol in the liver through interruption of HMG coenzyme A reductase. The dosage of lovastatin should be individualized depending on the desired and/or degree of serum cholesterol that is desired. Generally 10 to 80 mg of lovastatin per day should be administered by mouth depending on the response and the degree of reduction in serum cholesterol level that is indicated.

Example 2

A tablet having the following formula was prepared:

| | | |
|---|---|---|
| lovastatin | 12.11 wt % | 40.0 mg |
| Polyox WSR Coagulant, NF* | 4.54 wt % | 15.0 mg |
| Polyox WSR N 80, NF** | 17.71 wt % | 58.5 mg |
| lactose (anhydrous) | 51.13 wt % | 168.9 mg |
| sodium lauryl sulfate | 3.03 t % | 10.0 mg |
| silicon dioxide Fumed USP/NF | 0.45 wt % | 1.5 mg |
| butylated hydroxy anisole | 0.03 wt % | 0.10 mg |
| Myvaplex 600P*** | 1.82 wt % | 6.0 mg |
| Seal Coating: | | |
| Opadry Clear**** | 2.85 wt % | 9.4 mg |
| sodium chloride | 0.94 wt % | 3.1 mg |
| Inner Coating: | | |
| hydroxypropylmethylcell. phthal.55 | 2.29 wt % | 7.58 mg |
| talc | 0.79 wt % | 2.6 mg |
| acetyl tributyl citrate | 0.23 wt % | 0.75 mg |
| sugar, confectioners 6X micronized | 0.08 wt % | 0.27 mg |
| Outer Coating: | | |
| cellulose acetate | 1.00 wt % | 3.32 mg |
| Eudragit S 100 | 0.34 wt % | 1.13 mg |
| triacetin | 0.08 wt % | 0.27 mg |
| polyethylene glycol 400 | 0.08 wt % | 0.27 mg |
| sugar, confectioners 6X micronized | 0.50 wt % | 1.66 mg |
| | 100.0 wt % | 330.35 mg |

*polyethylene oxide Mw No av 5,000,000
**polyethylene oxide Mw No av 200,000
***glyceryl monostearate
****mixture containing hydroxypropyl methyl cellulose and polyethylene glycol
¹Eudragit S 100 (poly(methacrylicacid, methylmethacrylate, 1:2 ratio MW (No. Av. 135,000 - USP Type B)

Coated tablets were prepared using the general procedure of Example 1, except that an indentation was made on the tablet surface.

Example 3

A tablet having the following formula was prepared:

| | | |
|---|---|---|
| lovastatin | 12.14 wt % | 20.0 mg |
| Polyox WSR Coagulant, NF* | 4.55 wt % | 7.5 mg |
| Polyox WSR N 80, NF** | 17.76 wt % | 29.25 mg |
| lactose (anhydrous) | 51.30 wt % | 84.5 mg |
| sodium lauryl sulfate | 3.04 wt % | 5.0 mg |
| silicon dioxide Fumed USP/NF | 0.46 wt % | 0.75 mg |
| butylated hydroxy anisole | 0.03 wt % | 0.05 mg |
| Myvaplex 600P*** | 1.82 wt % | 3.0 mg |
| Seal Coating: | | |
| Opadry Clear**** | 3.42 wt % | 5.63 mg |
| sodium chloride | 1.14 wt % | 1.88 mg |
| Outer Coating: | | |
| cellulose acetate | 1.43 wt % | 2.36 mg |
| Eudragit S 100[1] | 0.49 wt % | 0.80 mg |
| triacetin | 0.11 wt % | 0.19 mg |
| polyethylene glycol 400 | 0.11 wt % | 0.19 mg |
| sugar, confectioners 6X micronized | 0.72 wt % | 1.18 mg |
| Overcoat: | | |
| hydroxypropylmethylcell. phthal.55 | 0.77 wt % | 1.27 mg |
| talc | 0.30 wt % | 0.49 mg |
| triacetin | 0.12 wt % | 0.20 mg |
| sugar, confectioners 6X micronized | 0.30 wt % | 0.49 mg |
| | 100.0 wt % | 146.73 mg |

*polyethylene oxide Mw No av 5,000,000
**polyethylene oxide Mw No av 200,000
***glyceryl monostearate
****mixture containing hydroxypropyl methyl cellulose and polyethylene glycol
[1]Eudragit S 100 (poly(methacrylic acid, methylmethacrylate, 1:2 ratio MW (No. Av. 135,000 - USP Type B)

The following describes the process of making the above described dosage form:
Step 1, the Tablet Core
(a) Granulation
1. Pass Polyox WSR N80, sodium lauryl sulfate and anhydrous lactose through a 30 mesh stainless steel screen.
2. Charge the screened materials and lovastatin (micronized) into a vertical granulator.
3. Dissolve butylated hydroxy anisole in ethanol.
4. Mix ethanol and purified water.
5. Pre-mix the powder mixture for 5 minutes.
6. Blend the powder mixture again, add the butylated hydroxyanisole solution and then the ethanol/water mixture.
7. Dry the granules at 45-50° C. until the moisture content is lower than 1.8 wt %.
8. Pass the granules through a 1575 mesh using a Comil.
Tabletting
1. Mix Cab-O-Sil and Polyox WSR NBO.
2. Pass the mixture of Cab-O-Sil and Polyox WSR N80 through a 24 mesh stainless steel screen with the Polyox WSR Coagulant'.
3. Blend the screen materials with lovastatin granules for 15 minutes.
4. Pass Myvaplex through a 30 mesh stainless steel screen and combine with the other screen materials.
5. Blend for five minutes.
6. Compress the blend into tablets (164.72 mg, round, standard concave, 17/6411 dia.) which contain 20 mg of lovastatin.
Seal Coating: Opadry Clear
1. Dissolve sodium chloride in purified water.
2. Disperse Opadry Clear into the sodium chloride solution.
3. Spray lovastatin tablets with the aqueous coating suspension using a coater.
Inner Coating: None
Outer Coating: Cellulose Acetate
1. Dissolve cellulose acetate and Eudragit S100 in acetone using a homogenizer.
2. Add polyethylene glycol 400, triactein and sugar to the solution and mix until a homogeneous dispersion is obtained.
3. Spray the coating suspension onto the tablets in a coater.
Overcoating: Hydroxypropyl Methylcellulose Phthalate 55
1. Dissolve hydroxypropyl methylcellulose phthalate 55 in acetone using a homogenizer.
2. Add acetyl tributyl citrate to the acetone solution and mix it with a homogenizer until a homogenized dispersion is obtained.
3. Add talc and sugar to the solution and mix it with a homogenizer until a homogenized dispersion is obtained.
4. Replace the homogenizer with a magnetic mixer and stir the coating mixture throughout the coating process.
5. Spray the Opadry Clear coated lovastatin tablets with the coating dispersion in a coater.

Example 4

A tablet having the following formula was prepared:

| | | |
|---|---|---|
| lovastatin | 12.20 wt % | 20.0 mg |
| Polyox WSR Coagulant, NF* | 4.57 wt % | 7.5 mg |
| Polyox WSR N 80, NF** | 17.84 wt % | 29.25 mg |
| lactose (anhydrous) | 51.53 wt % | 84.5 mg |
| sodium lauryl sulfate | 3.05 wt % | 5.0 mg |
| silicon dioxide Fumed USP/NF | 0.46% | 0.75 mg |
| butylated hydroxy anisole | 0.03 wt % | 0.05 mg |
| Myvaplex 600P*** | 1.83 wt % | 3.0 mg |
| Seal Coating: | | |
| Opadry Clear**** | 3.43 wt % | 5.63 mg |
| sodium chloride | 1.15 wt % | 1.88 mg |
| Inner Coating: None | | |
| Outer Coating: | | |
| cellulose acetate | 1.96 wt % | 3.21 mg |
| Eudragit S 100[1] | 0.66 wt % | 1.09 mg |
| acetyl tributyl citrate | 0.32 wt % | 0.52 mg |
| sugar, confectioners 6X micronized | 0.98 wt % | 1.61 mg |
| | 100.00 wt % | 163.99 mg |

*polyethylene oxide Mw No av 5,000,000
**polyethylene oxide Mw No av 200,000
***glyceryl monostearate
****mixture containing hydroxypropyl methyl cellulose and polyethylene glycol Coated tablets were prepared using the general procedure of Example 3 except that no inner coating was applied.

A comparison of Examples 2, 3 and 4 shows that the following was the weight of the coatings that were applied:

| | | |
|---|---|---|
| Example 2 | Inner Coating | 4 wt % |
| | Outer Coating | 2 wt % |
| | Over Coating | 0% |
| Example 3 | Inner Coating | 0% |
| | Outer Coating | 3 wt % |
| | Over Coating | 2.5% |
| Example 4 | Inner Coating | 0 wt % |
| | Outer Coating | 4 wt % |
| | Over Coating | 0 wt % |

FIG. 2 is a graph of in vitro dissolution data which shows the dissolution profiles of the formulations of Example 3, 4 and 5 in 2% sodium lauryl sulfate at pH 7.0 in NaH$_2$PO$_4$ buffer in a USP XXII Type II dissolution apparatus at 50 rpms at 37° C.

It is believed that administration of the above described micronized Lovastatin in these amounts will be particularly effective in inhibiting the biosynthesis of cholesterol in the liver through interruption of HMG coenzyme A reductase. The dosage of lovastatin should be individualized depending on the desired and/or degree of serum cholesterol that is desired. Generally 10 to 80 mg of lovastatin per day should be administered by mouth depending on the response and the degree of reduction in serum cholesterol level that is indicated.

Examples 5-7

In Examples 5-7, 40 mg lovastatin tablets were prepared using the general procedure of Example 1. The ingredients of Examples 5-7 are set forth in Table 2 below.

TABLE 2

Summary of Lovastatin Formulations

| Ingredient | Weight Percent | | |
|---|---|---|---|
| | Example 5 | Example 6 | Example 7 |
| Lovastatin (strength, mg) | 40 | 40 | 40 |
| Tablet Core | | | |
| 1. Lovastatin | 12.11 | 12.28 | 12.28 |
| 2. Lactose (Anhydrous) | 51.13 | 51.8 | 51.8 |
| 3. Polyox ® WSR Coagulant | 4.54 | 4.6 | 4.6 |
| 4. Polyox ® WSR N80 | 17.71 | 17.94 | 17.94 |
| 5. Sodium Lauryl Sulfate | 3.03 | 3.06 | 3.06 |
| 6. Glyceryl Monostearate | 1.82 | 1.84 | 1.84 |
| 7. Silicon Dioxide | 0.45 | 0.46 | 0.46 |
| 8. Butylated Hydroxyanisole | 0.03 | 0.02 | 0.02 |
| Seal Coat | | | |
| 1. Opadry Clear | 2.85 | 2.88 | 2.88 |
| 2. Sodium Chloride Powder | 0.94 | 0.96 | 0.96 |
| Inner Coat | | | |
| 1. HPMCP 55 | 2.29 | 1.61 | 1.61 |
| 2. Talc, USP | 0.79 | 0.55 | 0.55 |
| 3. Acetyltributyl Citrate | 0.23 | 0.16 | 0.16 |
| 4. Sugar, Micronized | 0.08 | 0.44 | 0.44 |
| Outer Coat | | | |
| 1. Cellulose Acetate | 1 | 0.7 | 0.7 |
| 2. Eudragit S100 | 0.34 | 0.24 | 0.24 |
| 3. Triacetin | 0.08 | 0.06 | 0.06 |
| 4. Polyethylene Glycol 400 | 0.08 | 0.6 | 0.6 |
| 5. Acetyltributyl Citrate | — | — | — |
| 6. Sugar, Micronized | 0.5 | 0.35 | 0.35 |
| Overcoat | | | |
| 1. HPMCP 55 | — | — | — |
| 2. Talc, USP | — | — | — |
| 3. Triacetin | — | — | — |
| 4. Sugar, Micronized | — | — | — |
| 5. Opadry Yellow | — | — | — |
| 6. Opadry Pink | — | — | — |
| Total Tablet Weight, % | 100 | 100 | 100 |

As can be ascertained from Table 2, Example 5 has the same composition as Example 2. However, the tablets of Example 5 do not contain the indentation in the tablet surface that was present in Example 2. Preliminary results of a single-dose study in healthy humans indicated that the indentation in the lovastatin formulation of Example 2 did not improve its pharmacokinetics. Because Example 5 provided the desired safety, efficacy and pharmacokinetic profiles in Studies 1-3 described in detail herein, two more clinical lots were made based on the composition and process of Example 5. Examples 6 and 7 are the two clinical lots made based on the composition of Example 5. A different coater (Glatt coater GPCG3) was used for the manufacturing of these two lots. Since the new coater had a better coating efficiency, less coating mixtures was required to achieve the same dissolution as that of Example 5. Considering the similarity of the dissolution profiles and the identical coating mixture composition, the "actual composition" of Examples 6 and 7 should be very similar to that of Example 5.

Examples 8-9

In Example 8, 20 mg lovastatin tablets were prepared. In Example 9, 10 mg lovastatin tablets were prepared. Both formulations were prepared using the general procedure of Example 1.

The composition of Example 9 is the same as Example 8, except that 10 mg of lactose has been used to replace 10 mg of drug substance (lovastatin).

The ingredients of Examples 8-9 are set forth in Table 3 below:

TABLE 3

Summary of Lovastatin Formulations

| Ingredients | Weight Percent | |
|---|---|---|
| | Example 8 | Example 9 |
| Lovastatin (strength, mg) | 20 | 10 |
| Tablet Core | | |
| 1. Lovastatin | 11.69 | 5.84 |
| 2. Lactose (Anhydrous) | 49.32 | 55.18 |
| 3. Polyox ® WSR Coagulant | 4.38 | 4.38 |
| 4. Polyox ® WSR N80 | 18.08 | 17.09 |
| 5. Sodium Lauryl Sulfate | 2.92 | 2.92 |
| 6. Blyceryl Monostearate | 1.75 | 1.75 |
| 7. Silicon Dioxide | 0.44 | 0.44 |
| 8. Butylated Hydroxyanisole | 0.02 | 0.01 |
| Seal Coat | | |
| 1. Opadry Clear | 2.74 | 2.74 |
| 2. Sodium Chloride Powder | 0.91 | 0.91 |
| Inner Coat | | |
| 1. HPMCP 55 | 2.21 | 2.21 |
| 2. Talc, USP | 0.76 | 0.76 |
| 3. Acetyltributyl Citrate | 0.22 | 0.22 |
| 4. Sugar, Micronized | 0.61 | 0.61 |
| Outer Coat | | |
| 1. Cellulose Acetate | 0.97 | 0.97 |
| 2. Eudragit S 100 | 0.33 | 0.33 |
| 3. Triacetin | 0.08 | 0.08 |
| 4. Polyethylene Glycol 400 | 0.08 | 0.08 |
| 5. Acetyltributyl Citrate | — | — |
| 6. Sugar, Micronized | 0.49 | 0.49 |
| Overcoat | | |
| 1. HPMCP 50 | — | — |
| 2. Talc | — | — |
| 3. Triacetin | — | — |
| 4. Sugar, Micronized | — | — |
| 5. Opadry Yellow | 3 | 3 |
| 6. Opadry Pink | — | — |
| Total Tablet Weight % | 100 | 100 |

Each of Examples 5-9 were evaluated by dissolution testing under the following conditions: USP apparatus 2 (paddles); medium: 2% SLS/sodium phosphate buffer (0.01M), pH 7.0, stir speed 50 rpm, and temperature 37° C. The dissolution profile for Examples 2 and 5-7 are illustrated in FIG. 3. The dissolution profiles for Examples 3, 4 and 8 are illustrated in FIG. 4. The dissolution profile for Example 9 is illustrated in FIG. 5. The dissolution profiles of Examples 5-7 and 2 are further provided in Table 4 below. The dissolution profiles of Examples 3, 4, 8 and 9 are further provided in Table 5 below.

TABLE 4

| Time (Hours) | Ex. 5 | Ex. 6 | Ex. 7 | Ex. 2 |
|---|---|---|---|---|
| 0 | 0 | 0 | 0 | 0 |
| 0.5 | 0 | 0 | 0 | 0 |
| 1 | 1 | 1 | 1 | 0 |
| 2 | 12 | 14 | 13 | 1 |
| 3 | 29 | 32 | 30 | 11 |
| 4 | 44 | 48 | 46 | 27 |
| 6 | 67 | 72 | 72 | 55 |
| 8 | 80 | 82 | 83 | 72 |
| 12 | 86 | 86 | 88 | 84 |
| 16 | 90 | 86 | 89 | 87 |
| 20 | 90 | 85 | 89 | 87 |

TABLE 5

| Time (Hours) | Ex. 3 | Ex. 4 | Ex. 8 | Ex. 9 |
|---|---|---|---|---|
| 0 | 0 | 0 | 0 | 0 |
| 0.5 | 5 | 0 | 0 | 0 |
| 1 | 15 | 0 | 0 | 1 |
| 2 | 36 | 4 | 4 | 6 |
| 4 | 70 | 18 | 33 | 39 |
| 6 | 86 | 37 | 65 | 67 |
| 8 | 90 | 54 | 82 | 80 |
| 12 | 92 | 78 | 89 | 86 |
| 16 | 99 | 85 | 92 | 88 |
| 20 | 99 | 87 | 92 | 89 |

Clinical Studies

Oral Pharmacokinetics

Studies were conducted to evaluate the formulations of Examples 5-9 (hereinafter collectively referred to as "Lovastatin XL™"). In certain of these studies, an immediate release tablet of lovastatin commercially available for more than 10 years (Mevacor®, Merck & Co., Inc.) was used as a reference standard.

Study No. 1 was a pharmacokinetics, safety and tolerability open-label, single dose, two-period crossover study of 40 mg Lovastatin XL tablets (Example 5) in comparison to Mevacor. There were 8 healthy male volunteers. The dose of Lovastatin XL and Mevacor was administered at 6:30 p.m., immediately after dinner.

Study No. 2 was a safety, pharmacokinetics and effect of food open-label, single dose, three-period crossover study comparing Lovastatin XL tablets (Example 5) to Mevacor. There were 9 healthy male volunteers. The dose of Lovastatin XL was administered at 8:00 a.m. (fasting), 8:00 a.m. immediately after breakfast (fed conditions), in comparison to Mevacor administered at 8:00 a.m., immediately after breakfast.

Study No. 3 examined the safety and pharmacokinetics of Lovastatin XL tablets (Example 5 and Example 2) in an open-label, single-dose, two-period crossover. There were 6 healthy male volunteers. The doses of Lovastatin XL were administered at 8 a.m., immediately after breakfast.

Study No. 4 was a multiple-dose, safety, tolerability, efficacy, pharmacodynamics and pharmacokinetics single-blind, 4-week active treatment, 2-period cross-over study with a 4-week diet/placebo run-in period in which 40 mg Lovastatin XL tablets (Example 5) were compared to Mevacor 40 mg tablets. Patients had a diet/placebo run-in period of 4 weeks prior to randomization to the active treatment. A total of 24 patients were randomized to receive 40 mg/day of Lovastatin XL, or 40 mg/day of Mevacor once daily in active treatment Period I and was switched to the alternate treatment drug in Period II. The Lovastatin XL tablets were administered on a once-daily basis for 4 weeks at about 10:00 p.m. The Mevacor tablets were administered once daily for 4 weeks at about 6 p.m., immediately after dinner. There was a two week placebo washout period between treatments. Of the 24 patients with hypercholesterolemia, 12 were male and 12 were female, and 13 of the subjects participated in the pharmacokinetic substudy. The results are summarized in Table 6.

Study No. 5 examined the oral pharmacokinetics, pharmacodynamics and safety of 10 mg, 20 mg and 40 mg Lovastatin XL tablets (Examples 9, 8 and 5, respectively). The study design was single-dose, 3-period cross-over, with 8 healthy male volunteers. Each of these dosages were administered at bedtime (about 10:00 p.m.).

Figure 8:
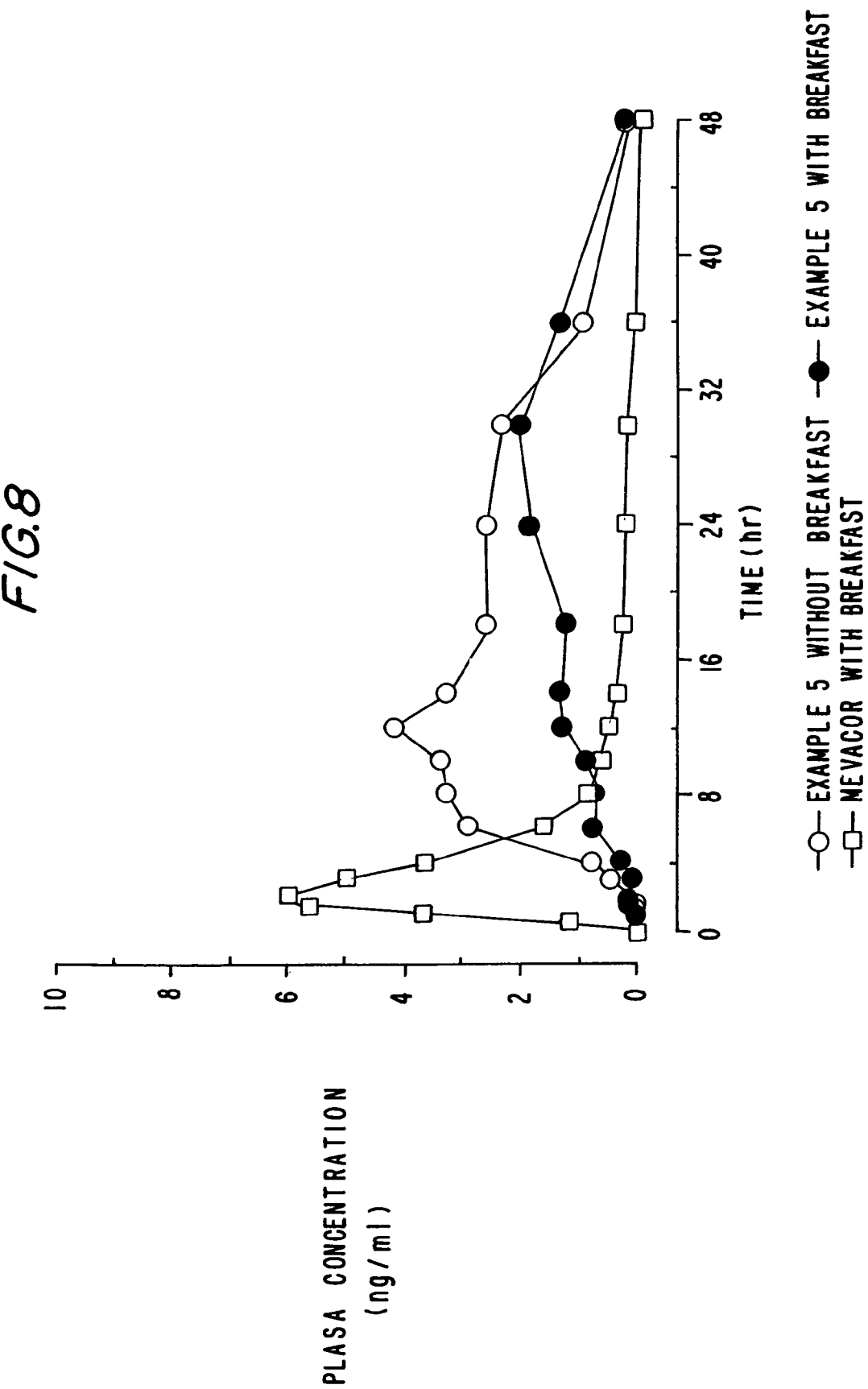
FIG. 8 is a graph of comparative data which shows mean (±SD) plasma concentration time profiles of lovastatin in healthy subjects (n=9) following a single oral dose in the morning of a conventional immediate release dose of 40 mg of lovastatin with breakfast and an extended release 40 mg dose of lovastatin according to the invention (Example 5) with and without breakfast.
Figure 9:
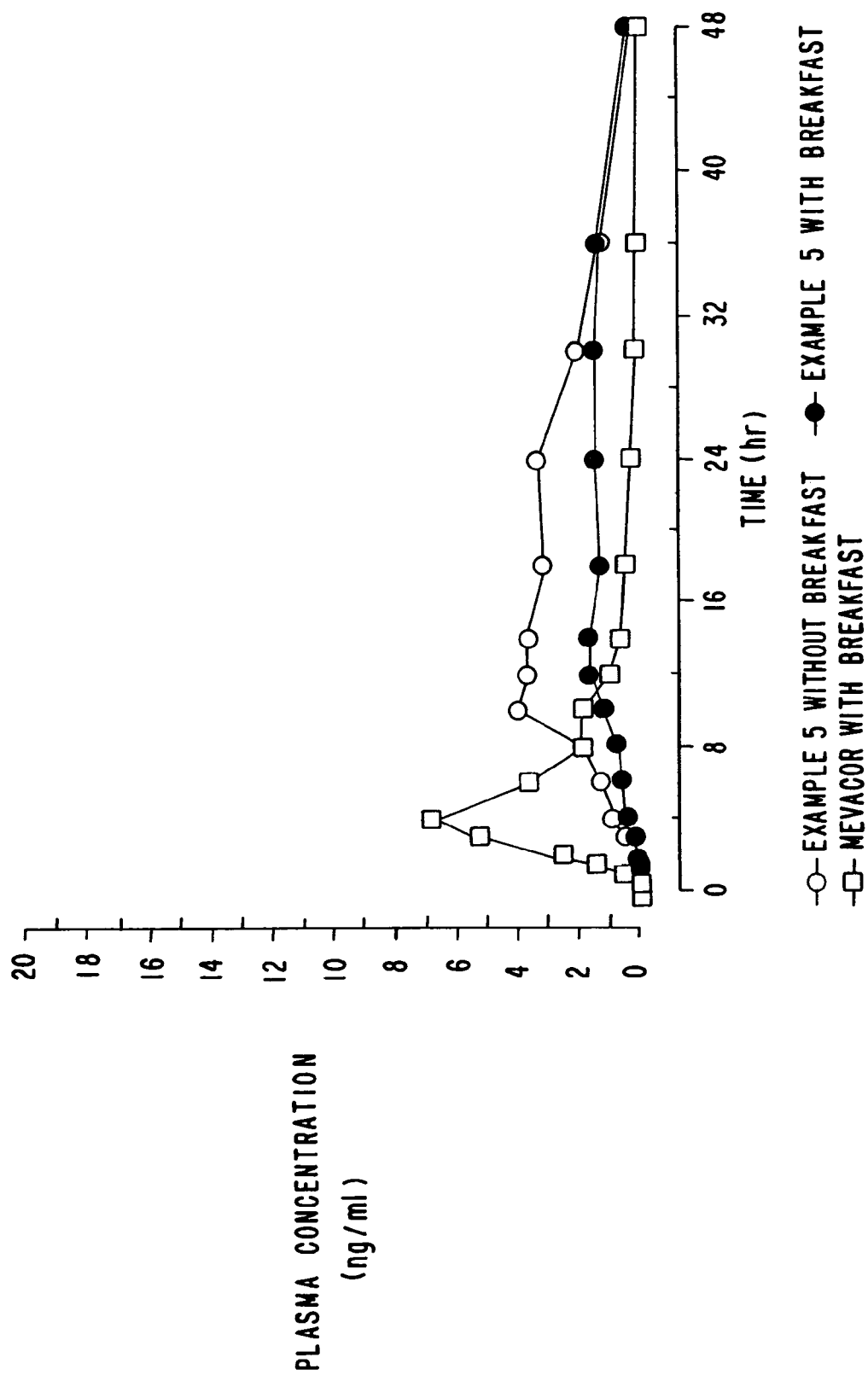
FIG. 9 is a graph of comparative data which shows mean (±SD) plasma concentration time profiles of lovastatin acid in healthy subjects (n=9) following a single oral dose in the morning of a conventional immediate release dose of 40 mg of lovastatin with breakfast and an extended release 40 mg dose of lovastatin according to the invention (Example 5) with and without breakfast.

Tables 6 and 7 provide mean pharmacokinetic values (for lovastatin and lovastatin acid, respectively) both Lovastatin XL and Mevacor for Study Nos. 1-5. Table 8 provides mean AUC and $C_{max}$ ratios for the 40 mg tablets in Study No. 4. Table 9 provides pharmacokinetic data (mean AUC and $C_{max}$ ratios) for Lovastatin XL 40 mg doses for Study Nos 1, 2 and 5. FIG. 6 is a graph of Study 1 of comparative data which shows mean (±SD) plasma concentration time profiles of lovastatin in healthy subjects (n=8) following a single oral dose of a conventional immediate release dose of 40 mg of lovastatin and an extended release 40 mg dose of lovastatin according to the invention Example 5). FIG. 7 is a graph of Study 1 of comparative data which shows mean (±SD) plasma concentration time profiles of lovastatin acid in healthy subjects (n=8) following a single oral dose of a conventional immediate release dose of 40 mg of lovastatin and an extended release 40 mg dose of lovastatin according to the invention (Example 5). FIG. 8 is a graph of Study 2 comparative data which shows mean (±SD) plasma concentration time profiles of lovastatin in healthy subjects (n=9) following a single oral dose in the morning of a conventional immediate release dose of 40 mg of lovastatin with breakfast and an extended release 40 mg dose of lovastatin according to the invention (Example 5) with and without breakfast. FIG. 9 is a graph of Study 2 of comparative data which shows mean (±SD) plasma concentration time profiles of lovastatin acid in healthy subjects (n=9) following a single oral dose in the morning of a conventional immediate release dose of 40 mg of lovastatin with breakfast and an extended release 40 mg dose of lovastatin according to the invention (Example 5) with and without breakfast.

The mean AUC values for lovastatin acid, active and total inhibitors at steady state were similar for both Lovastatin XL and Mevacor (Tables 7 and 8). From the results of these studies, it was found that when compared to Mevacor and regardless of dosing time, Lovastatin XL had higher bioavailability of inactive prodrug (lovastatin), as reflected by mean AUC values and by geometric mean AUC ratios of lovastatin which were greater than unity, after administration of a single dose (Table 6). Geometric AUC ratios for the acid were close to unity (Table 7).

The mean AUC values for lovastatin acid, active and total inhibitors at steady state were similar for both Lovastatin XL and Mevacor (Tables 7 and 8). From the results of these studies, it was found that when compared to Mevacor and regardless of dosing time, Lovastatin XL had higher bioavailability of inactive prodrug (lovastatin), as reflected by mean AUC values and by geometric mean AUC ratios of lovastatin which were greater than unity, after administration of a single dose (Table 9). Geometric AUC ratios for the acid were close to unity (Table 9).

Efficacy

Study No. 4 was designed to evaluate the safety, efficacy, pharmadynamics, pharmacokinetics, and tolerability of Lovastatin XL relative to MEVACOR after multiple-dose treatment in patients with fasting plasma LDL-cholesterol levels between 130 and 250 mg/dl and triglyceride levels below 350 mg/dl. This study had a single-center, single-blind, randomized, two-way crossover design. Patients had a diet/placebo run-in period of 4 weeks prior to randomization to the active treatment. A total of 24 patients were randomized to receive 40 mg/day of lovastatin to the alternate treatment drug in Period II. During the active treatment periods, patients were instructed to take Lovastatin XL daily in the evening at approximately 10:00 p.m. for 4 weeks, or MEVACOR daily with the evening meal (about 6:00 p.m.) for 4 weeks. There was a two-week placebo washout period between treatments.

Figure 10:
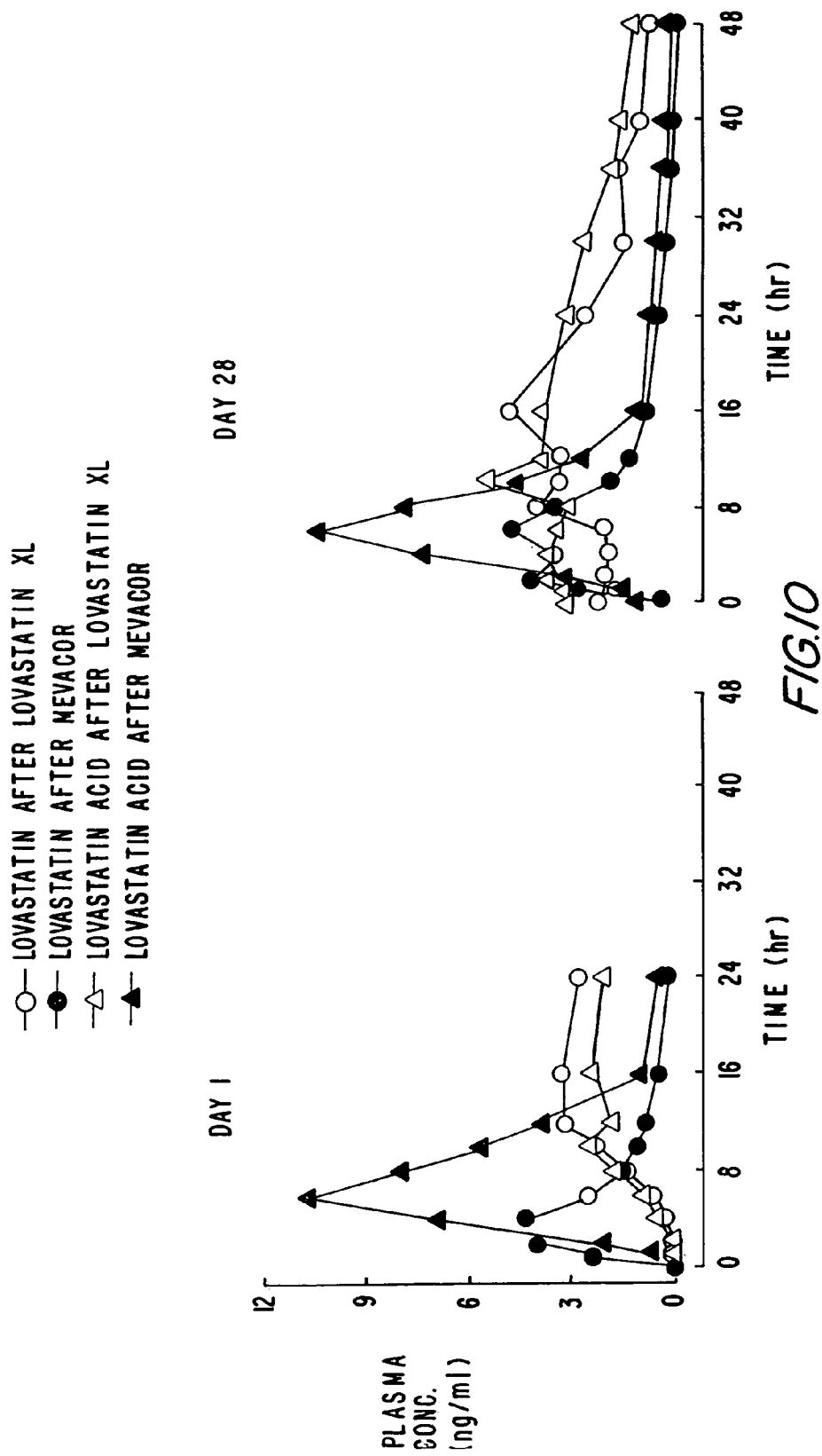
FIG. 10 is a graph of the mean plasma concentration-time profiles of lovastatin and lovastatin acid in patients (n=12) after multiple-dose administration of 40 mg Lovastatin XL and a conventional 40 mg immediate release dose of lovastatin (Study No. 5, Day 1 and Day 28).
Figure 11:
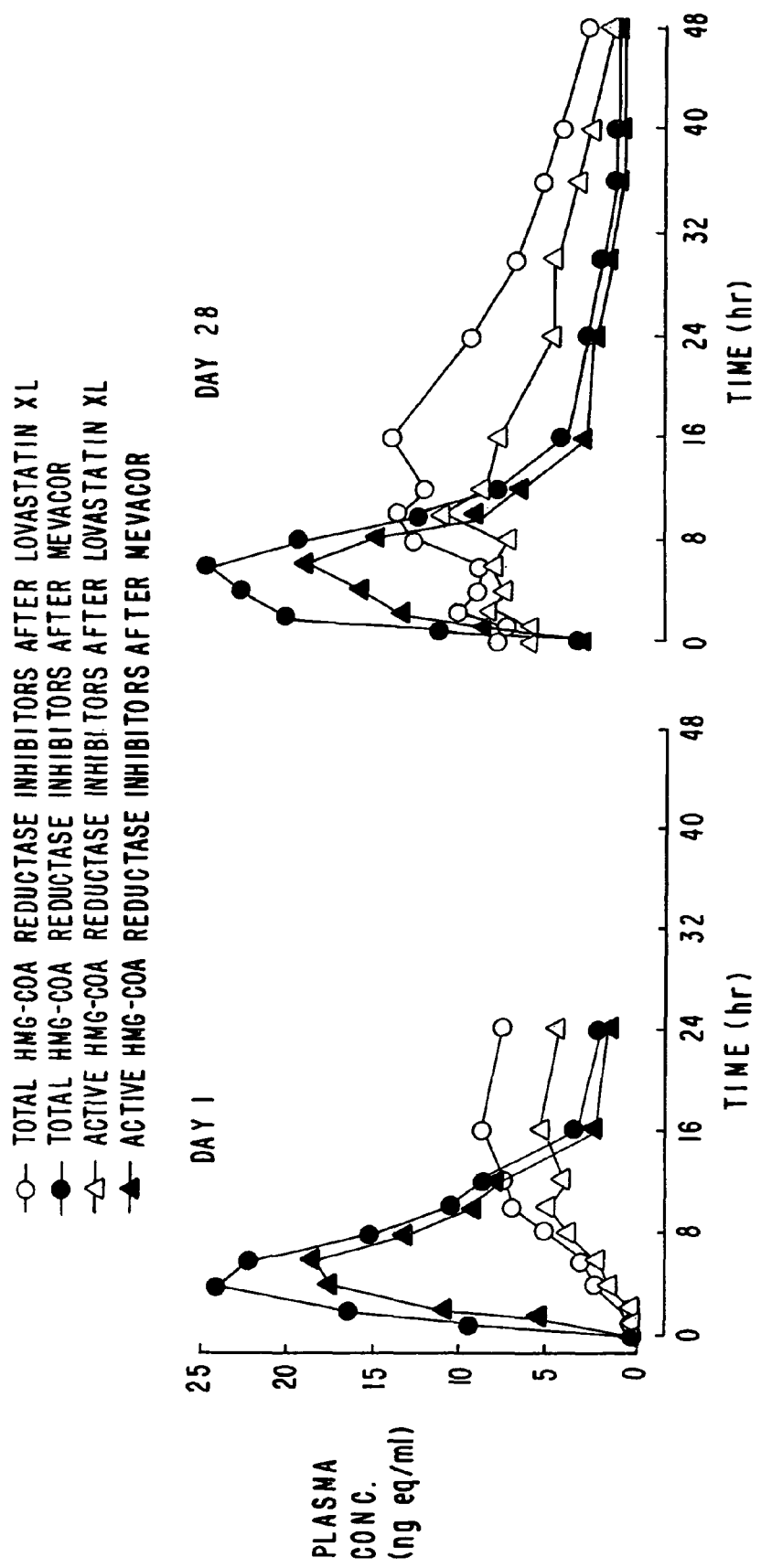
FIG. 11 is a graph of the mean plasma concentration-time profiles of total and active inhibitors of HMG-CoA Reductase in patients (n=12) after multiple-dose administration of 40 mg Lovastatin XL and a conventional 40 mg immediate release dose of lovastatin (Study No. 4 Day 1 and Day 28).

The multiple-dose pharmacokinetics of Lovastatin XL studied in patients in Study No. 4 are depicted in FIGS. 10 and 11 and in Table 11. FIG. 10 is a graph of the mean plasma concentration-time profiles of lovastatin and lovastatin acid in patients (n=12) after multiple-dose administration of 40 mg Lovastatin XL and a conventional 40 mg immediate release dose of lovastatin (Study No. 4, Day 1 and Day 28). FIG. 11 is a graph of the mean plasma concentration-time profiles of total and active inhibitors of HMG-CoA Reductase in patients (n=12) after multiple-dose administration of 40 mg Lovastatin XL and a conventional 40 mg immediate release dose of lovastatin (Study No. 4, Day 1 and Day 28).

The mean plasma concentration-time profiles of lovastatin, lovastatin acid, and total and active inhibitors of HMG-CoA reductase following administration of 40 mg/day of Lovastatin XL for four weeks exhibited extended release characteristics, as depicted in FIGS. 10 and 11 and in Table 11. Table 12 provides the Least Squares Means–% change in LDL-Cholesterol, HDL-Cholesterol, Total Cholesterol and Triglycerides of Study No. 4. The increased systemic bioavailability of lovastatin when administered as the XL formulation was not accompanied by increased bioavailability of lovastatin acid, active or total inhibitors. The mean plasma concentration-time profiles of these compounds following administration of 40 mg/day of Mevacor for four weeks exhibited immediate-release characteristics. No accumulation was observed with Mevacor. As can be ascertained from these results, the accumulation of lovastatin and its latent and active metabolites after chronic once-daily administration of Lovastatin XL was approximately 1.4- to 2-fold. The primary efficacy endpoints defined by the protocol were the changes from baseline of blood lipid values at weeks 3 and 4 (combined) of treatment. Values were also calculated for Weeks 3 and 4 individually and were not combined if the treatment-by-time interaction was significant. Results of this study demonstrated that Lovastatin XL lowered LDL-cholesterol 4.4 percentage points more (p=0.0605) than MEVACOR at Week 3, 3.6 percentage points more (p=0.0737) at Week 4, and 3.9 percentage points more (p=0.0435) when Weeks 3 and 4 are combined (Table 9). When compared with MEVACOR, mean Lovastatin XL HDL-cholesterol values increased 2.7 percentage points more (p=0.2588) at Week 3 and 3.0 percentage points more (p=0.2741) at Week 4 of each treatment period, and 3.0 percentage points more (p=0.1402) with Week 3 and 4 combined. Mean Lovastatin XL total cholesterol values decreased 3.4 percentage points more (p=0.0245) at Week 3, 1.7 percentage points more (p=0.3422) at Week 4, and 2.5 percentage points more (p=0.0721) with Week 3 and 4 combined. Mean Lovastatin XL triglyceride values decreased 101.2 percentage points more (p=0.1067) at Week 3, but increased 3.1 percentage points more (p=0.5297) at Week 4. Lovastatin XL, at 40 mg daily, produced 41 percent lowering in mean LDL-cholesterol. The magnitude of this reduction was 3.9 percentage points greater (p=0.0435, based on combined Weeks 3 and 4 data) than was produced by an equal dose of MEVACOR. Based on the well-recognized dose-response relationship that doubling the dose of a statin produces approximately a 6 to 7 percentage point further decline in LDL-cholesterol, the 3.9 percentage point differential observed in this trial would, if reproducible, translate to the response expected from a dosage equivalent of MEVACOR of more than 60 mg.

TABLE 6

Mean ± SD Values of $AUC$, $C_{max}$ and $T_{max}$ of Lovastatin

| Study No. | Dosing Time/Dose | n | $AUC_{0-48\ hr}$ (ng · hr/ml) Lovastatin XL | $AUC_{0-48\ hr}$ (ng · hr/ml) MEVACOR | $C_{max}$ (ng/ml) Lovastatin XL | $C_{max}$ (ng/ml) MEVACOR | $T_{max}$ (hr) Lovastatin XL | $T_{max}$ (hr) MEVACOR |
|---|---|---|---|---|---|---|---|---|
| 1 | with Dinner/Single Dose | 8 | 33.9 ± 11.8* | 26.6 ± 17.0* | 3.15 ± 1.24 | 6.13 ± 2.56 | 15.5 ± 5.1 | 2.1 ± 0.6 |
| 2 | with Breakfast/Single Dose | 9 | 54.7 ± 27.7 | 33.1 ± 10.4 | 3.09 ± 1.48 | 6.72 ± 2.75 | 24.0 ± 7.9 | 2.4 ± 0.9 |
|  | Fasting/Single Dose | 9 | 90.5 ± 50.0 | — | 4.86 ± 1.99 | — | 11.1 ± 5.8 | — |
| 3 | with Breakfast/Single Dose | 6 | 78.7 ± 37.9 | — | 4.01 ± 2.47 | — | 16.3 ± 6.4 | — |
| 4 | Bedtime/Single Dose | 12 | 49.9 ± 23.5* | — | 4.0 ± 2.0 | — | 16.9 ± 6.3 | — |
|  | with Dinner/Single Dose | 12 | — | 33.7 ± 21.6* | — | 6.7 ± 4.0 | — | 3.0 ± 1.5 |
|  | Bedtime/Multiple Dose | 12 | 76.6 ± 36.9* | — | 5.5 ± 2.5 | — | 14.2 ± 7.6 | — |
|  | with Dinner/Multiple Dose | 12 | — | 44.7 ± 46.2* | — | 7.8 ± 8.1 | — | 3.3 ± 2.2 |
| 5 | Bedtime/Single Dose (40 mg) | 8 | 53.94 ± 35.55 | — | 4.03 ± 3.02 | — | 14.3 ± 4.5 | — |
| 5 | Bedtime/Single Dose (20 mg) | 8 | 34.1 ± 13.7 | — | 2.03 ± 0.65 | — | 13.5 ± 2.8 | — |
| 5 | Bedtime/Single Dose (10 mg) | 8 | 14.59 ± 7.78 | — | 1.04 ± 0.43 | — | 12.8 ± 2.1 | — |

*$AUC_{0-24\ hr}$

TABLE 7

Mean ± SD Values of AUC, $C_{max}$ and $T_{max}$ of Lovastatin Acid

| Study No. | Dosing Time/Dose | n | $AUC_{0-48\,hr}$ (ng·hr/ml) Lovastatin XL | MEVACOR | $C_{max}$ (ng/ml) Lovastatin XL | MEVACOR | $T_{max}$ (hr) Lovastatin XL | MEVACOR |
|---|---|---|---|---|---|---|---|---|
| 1 | with Dinner/Single Dose | 8 | 47.5 ± 18.9* | 42.2 ± 20.3* | 4.64 ± 1.89 | 6.45 ± 4.09 | 13.8 ± 3.8 | 3.9 ± 1.0 |
| 2 | with Breakfast/Single Dose | 9 | 50.3 ± 35.6 | 41.6 ± 35.1 | 2.50 ± 1.45 | 6.88 ± 5.81 | 20.9 ± 7.8 | 2.4 ± 0.9 |
|   | Fasting/Single Dose | 9 | 91.2 ± 59.6 | — | 4.90 ± 2.32 | — | 14.7 ± 5.9 | — |
| 3 | with Breakfast/Single Dose | 6 | 42.8 ± 12.9 | — | 2.52 ± 0.97 | — | 18.7 ± 4.5 | — |
| 4 | Bedtime/Single Dose | 12 | 38.6 ± 31.4* | — | 2.9 ± 2.5 | — | 14.5 ± 5.3 | — |
|   | with Dinner/Single Dose | 12 | — | 84.1 ± 63.1* | — | 11.7 ± 6.9 | — | 5.7 ± 1.2 |
|   | Bedtime/Multiple Dose | 12 | 87.1 ± 67.2* | — | 5.8 ± 4.8 | — | 11.8 ± 7.4 | — |
|   | with Dinner/Multiple Dose | 12 | — | 82.5 ± 60.3* | — | 11.9 ± 10.2 | — | 5.3 ± 1.0 |
| 5 | Bedtime/Single Dose (40 mg) | 8 | 71.25 ± 61.29 | — | 3.85 ± 2.68 | — | 13.0 ± 7.7 | — |

*$AUC_{0-24\,hr}$

TABLE 8

Mean ± SD Value of AUC, Cmax and Tmax of Total and Active HMG-CoA Reductase Inhibitors

| Study No. | Dosing Time/Dose | n | $AUC_{0-48\,hr}$ (ng·hr/ml) Lovastatin XL | MEVACOR | $C_{max}$ (ng/ml) Lovastatin XL | MEVACOR | $T_{max}$ (hr) Lovastatin XL | MEVACOR |
|---|---|---|---|---|---|---|---|---|
| | Total HMG-CoA Reductase Inhibitors | | | | | | | |
| 4 | Bedtime/Single Dose | 12 | 136.3 ± 73.3 | — | 10.5 ± 5.8 | — | 17.3 ± 4.3 | — |
|   | with Dinner/Single Dose | 12 | — | 226.9 ± 100.4 | — | 31.4 ± 9.4 | — | 3.7 ± 2.3 |
|   | Bedtime/Multiple Dose | 12 | 262.6 ± 159.4 | — | 17.3 ± 8.1 | — | 13.2 ± 9.4 | — |
|   | with Dinner/Multiple Dose | 12 | — | 251.6 ± 154.1 | — | 36.2 ± 20.7 | — | 3.9 ± 2.0 |
| | Active HMG-CoA Reductase Inhibitors | | | | | | | |
| 4 | Bedtime/Single Dose | 12 | 83.3 ± 44.7 | — | 6.4 ± 4.3 | — | 15.2 ± 4.9 | — |
|   | with Dinner/Single Dose | 12 | — | 178.9 ± 82.9 | — | 22.4 ± 6.6 | — | 4.4 ± 2.4 |
|   | Bedtime/Multiple Dose | 12 | 171.3 ± 122.9 | — | 13.4 ± 9.1 | — | 9.5 ± 3.3 | — |
|   | with Dinner/Multiple Dose | 12 | — | 185.9 ± 100.4 | — | 26.6 ± 14.2 | — | 4.2 ± 2.1 |

TABLE 9

Mean AUC and Cmax Ratios (40-mg Dose) [Study Nos. 1, 2 and 4]

| Dosing Time/Dose | Mean $AUC_{0-24\,hr}$ Ratio[a] Lovastatin | Lovastatin Acid | Total Inhibitors | Active Inhibitors | Mean $C_{max}$ Ratio[a] Lovastatin | Lovastatin Acid | Total Inhibitors | Active Inhibitors |
|---|---|---|---|---|---|---|---|---|
| Breakfast/Single Dose (Study 2) | 1.56[b] | 1.24[b] | — | — | 0.76 | 0.76 | — | — |
| Dinner Time/Single Dose (Study 1) | 1.41 | 1.14 | — | — | 0.51 | 0.77 | — | — |
| Bedtime (XL) & Dinner (MEVACOR)/Single Dose (Study 4) | 1.49 | 0.46 | 0.56 | 0.46 | 0.62 | 0.23 | 0.29 | 0.25 |
| Bedtime (XL) & Dinner (MEVACOR)/Multiple Dose (Study 4) | 1.91 | 0.86 | 0.96 | 0.84 | 0.84 | 0.43 | 0.48 | 0.47 |

[a] Ratio = Lovastatin XL/MEVACOR
[b] Mean $AUC_{0-48\,hr}$ Ratio

TABLE 10

Effect of Food on Pharmacokinetics of Lovastatin and Lovastatin Acid [Study No. 2]

| Treatment | $AUC_{0\text{-}48\,hr}$ (ng · hr/ml) | $C_{max}$ (ng/ml) | $T_{lag}$ (hr) | $T_{max}$ (hr) |
|---|---|---|---|---|
| Lovastatin | | | | |
| Lovastatin XL without breakfast | 90.0 ± 50.0 | 4.86 ± 1.99 | 1.9 ± 0.6 | 11.1 ± 5.8 |
| Lovastatin XL after breakfast | 54.7 ± 27.7 | 3.09 ± 1.48 | 2.7 ± 1.1 | 24.0 ± 7.9 |
| Geometric Mean Ratio[a] | 0.60 | 0.61 | — | — |
| Lovastatin Acid | | | | |
| Lovastatin XL without breakfast | 91.2 ± 59.6 | 4.90 ± 2.32 | 2.1 ± 0.4 | 14.7 ± 5.9 |
| Lovastatin XL after breakfast | 50.3 ± 35.6 | 2.50 ± 1.45 | 2.8 ± 1.0 | 20.9 ± 7.8 |
| Geometric Mean Ratio[a] | 0.54 | 0.49 | — | — |

[a]Ratio = Lovastatin XL after breakfast/Lovastatin XL without breakfast

Dose Proportionality

Figure 12:
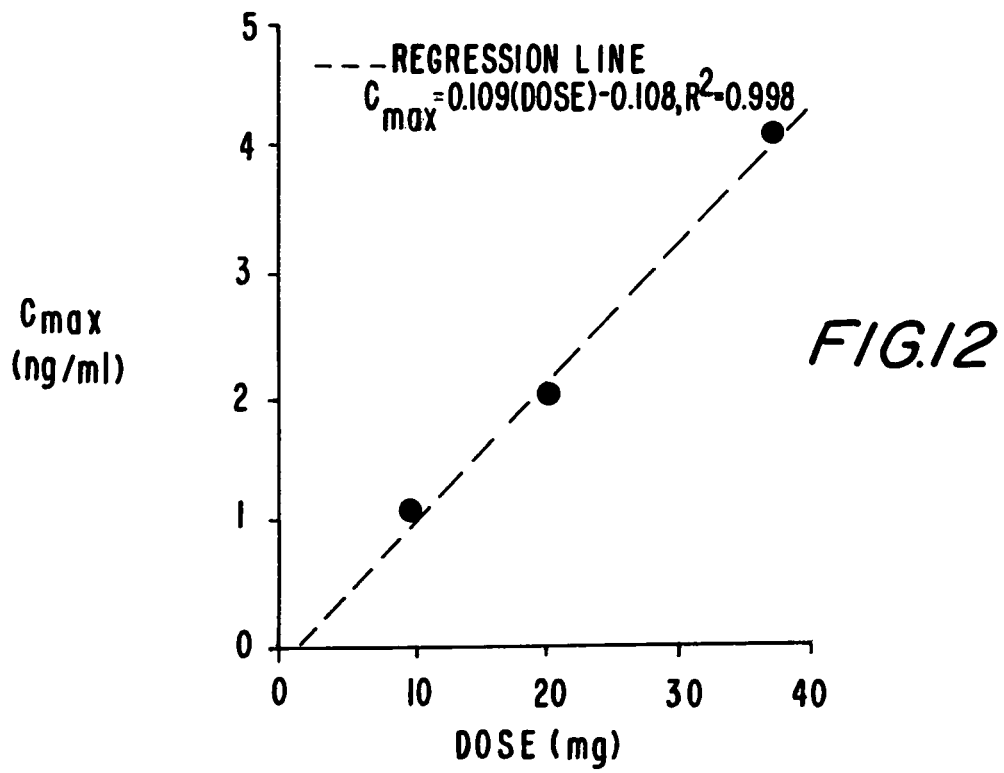
FIG. 12 is a graph of a regression line depicting $C_{max}$ plotted against dose for Study No. 5.
Figure 13:
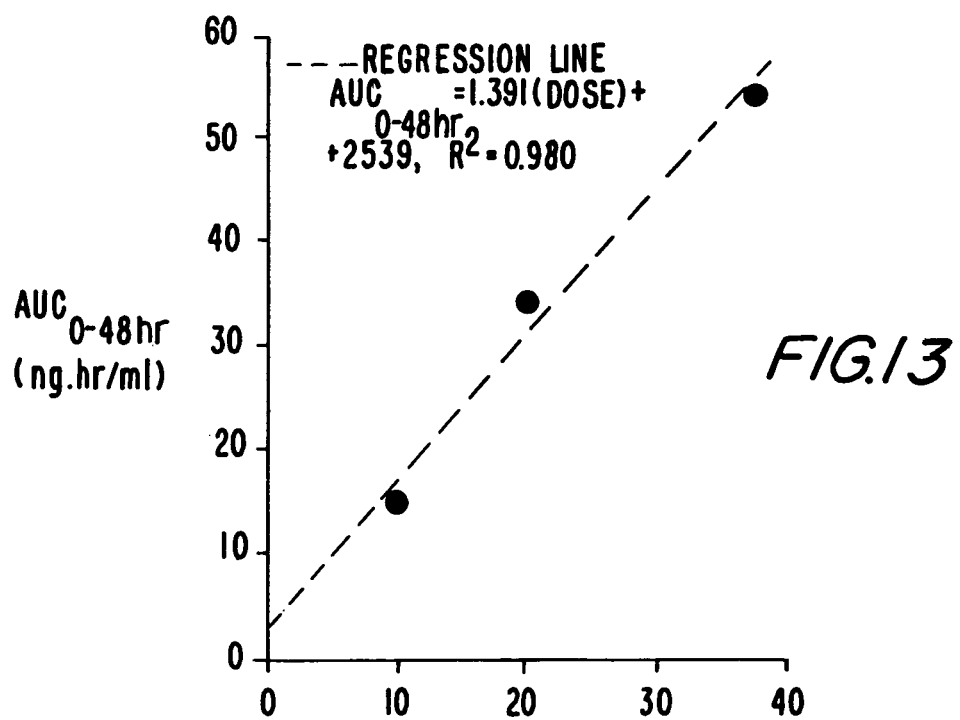
FIG. 13 is a graph of a regression line depicting $AUC_{0-48hr}$ plotted against dose for Study No. 5.

Study No. 5 was conducted in healthy volunteers receiving separately single oral doses of 10, 20 and 40 mg of Lovastatin XL. Results of this study indicated that, as the dose of Lovastatin XL increased from 10 to 40 mg, the $AUC_{0\text{-}48hr}$ and $C_{max}$ values of lovastatin appeared to increase linearly (see results for Study No. 5 depicted in Table 6). FIG. 12 is a graph of a regression line depicting $C_{max}$ plotted against dose for Study No. 5. FIG. 13 is a graph of a regression line depicting $AUC_{0\text{-}48hr}$ plotted against dose for Study No. 5.

TABLE 11

Mean ± SD (n = 12) Values of AUC0-24 hr (ng · hr/ml or ng eq · hr/ml) and Cmax (ng/ml or ng eq/ml) after Multiple Oral Doses of Lovastatin XL [Study No. 4]

| | $AUC_{0\text{-}24\,hr}$ | | | $C_{max}$ | | |
|---|---|---|---|---|---|---|
| | Day 1 | Day 28 | R* | Day 1 | Day 28 | R* |
| Lovastatin | 49.9 ± 23.5 | 76.6 ± 36.9 | 1.48 | 4.0 ± 2.0 | 5.5 ± 2.5 | 1.36 |
| Lovastatin acid | 38.7 ± 31.4 | 87.1 ± 67.2 | 1.88 | 2.9 ± 2.5 | 5.8 ± 4.8 | 1.70 |
| Total of inhibitors of HMG-CoA reductase | 136.3 ± 73.3 | 262.6 ± 159.4 | 1.82 | 10.5 ± 5.8 | 17.3 ± 8.1 | 1.71 |
| Active inhibitors of HMG-CoA reductase | 83.3 ± 44.7 | 171.3 ± 122.9 | 1.86 | 6.4 ± 4.3 | 13.4 ± 9.1 | 2.06 |

*R - Geometric mean ratio of $C_{max}$ or $AUC_{0\text{-}24\,hr}$ on Day 28 to that on Day 1.

TABLE 12

Least Squares Means
% Change in LDL-Cholesterol, HDL-Cholesterol, Total Cholesterol, and Triglycerides [Study No. 4]

| Parameter | Week | n | Lovastatin XL | MEVACOR | Difference | p-value |
|---|---|---|---|---|---|---|
| LDL-C | 3 | 24 | −40.60 | −36.19 | −4.41 | .0605 |
| | 4 | 22 | −42.48 | −38.86 | −3.62 | .0737 |
| | 3&4 | 24 | −41.32 | −37.45 | −3.87 | .0435* |
| HDL-C | 3 | 24 | +7.73 | +5.06 | +2.67 | .2588 |
| | 4 | 22 | +8.81 | +5.77 | +3.04 | .2741 |
| | 3&4 | 24 | +8.19 | +5.18 | +3.01 | .1402 |
| Total-C | 3 | 24 | −27.80 | −24.44 | −3.36 | .0245* |
| | 4 | 22 | −29.27 | −27.60 | −1.67 | .3422 |
| | 3&4 | 24 | −28.48 | −25.99 | −2.48 | .0721 |
| Trigylcerides | 3 | 24 | −20.53 | −10.33 | −10.20 | .1067 |
| | 4 | 22 | −21.02 | −24.14 | +3.12 | .5297 |

*Significant at p < 0.05

Analytical Methods

Concentrations of lovastatin and lovastatin acid in plasma samples from the first single-dose, safety and pharmacokinetic study [Study No. 1] were determined by a LC/MS/MS method. The internal standards (mevastatin and mevastatin β-hydroxyacid) were added to each plasma sample (1 ml). Each sample was extracted on a SPEC-Plus C18 disc, which was previously conditioned with methanol and water. The disc was then washed with water and formic acid. The analytes were eluted with 70:30 (v:v) methanol:water and 75:25 (v:v) acetonitrile:ethyl acetate. The eluate was then evaporated to dryness and reconstituted in 50 μl of mobile phase (sodium acetate in acetonitrile/water). The sample was injected onto a SCIEX API III-Plus LC/MS/MS equipped with a short C18 HPLC column. The peak area of the m/z 421.3→319.3 product ion of lovastatin acid was measured against the m/z 407.6→305.0 product ion of the internal standard (mevastatin β-hydroxyacid) using negative ion MRM mode. The peak area of the m/z 427.4→325.0 product ion of lovastatin was measured against the m/z 413.2→311.0 product ion of the internal standard (mevastatin) using positive ion MRM mode. Quantitation was performed using a weighted (1/concentration$^2$) linear least squares regression line generated from plasma calibration standards. The standard lines for lovastatin and lovastatin acid were linear over the concentration range of 0.1-50 ng/ml. The interday precision and accuracy values were 3.7-24.3% relative standard deviation and within 13%, respectively.

Concentrations of lovastatin and lovastatin acid in plasma samples from Study Nos. 2-5 were determined by a LC/MS/MS method. The pH of each plasma sample was adjusted with ammonium formate buffer. Lovastatin, lovastatin acid and their corresponding internal standards ($d_5$-lovastatin and $d_5$-lovastatin acid) were extracted using SPE cartridges and eluted with 75% methanol followed by acetonitrile. The extract was dried under nitrogen, reconstituted and injected onto a LC/MS/MS. The peak area of the m/z 423.2→303.2 product ion of lovastatin acid was measured against the m/z 428.2→303.2 product ion of the internal standard (d$_5$-lovastatin acid) using MRM mode. The peak area of the m/z 405.2→285.2 product ion of lovastatin was measured against the m/z 410.2→285.2 product ion of the internal standard (d$_5$-lovastatin) using MRM mode. Quantitation was performed using a weighted (1/concentration) linear least squares regression line generated from plasma calibration standards. The standard lines for lovastatin and lovastatin acid were linear over the concentration range of 0.1-20 ng/ml. The interday precision and accuracy values were 6.4-9.3% relative standard deviation and within 7%, respectively.

An enzymatic assay method was used to determine concentrations of active inhibitors (lovastatin acid+active metabolites of lovastatin) and total inhibitors (lovastatin+ lovastatin acid+latent and active metabolites of lovastatin) of HMG-CoA reductase inhibitors in plasma samples from the multiple-dose study [Study No. 4]. An aliquot of each sample was subjected to alkaline hydrolysis to determine the concentration of total inhibitors. Concentrations of active inhibitors were determined in unhydrolyzed samples. The inhibitory activity was measured against lovastatin acid as a standard. Lovastatin acid was used in its ammonium salt form and all results were expressed as nanogram equivalent per milliliter. The standard curves for total and active inhibitors were over the concentration range of 0.5-100 ng eq/ml. The interday precision and accuracy values were 2.64-9.84% relative standard deviation and within 12.5%, respectively.

CONCLUSIONS

1. The bioavailability of Lovastatin XL relative to MEVACOR, in terms of $AUC_{0-24hr}$ or $AUC_{0-48hr}$ ratio of lovastatin, is greater than 100% after single-dose administration. The same is true at steady state. However, the relative bioavailability of Lovastatin XL to MEVACOR at steady state, in terms of $AUC_{0-24hr}$ ratio of lovastatin acid or active or total inhibitors of HMG-CoA reductase, is close to or less than 100%.
2. Together with low $C_{max}$ values, the relative bioavailability of Lovastatin XL indicates that the systemic exposure of patients to active drug and metabolites of lovastatin as well as total inhibitors of HMG-CoA reductase after administration of Lovastatin XL is not higher than that after administration of MEVACOR.
3. Administration of Lovastatin XL following a high-fat breakfast decreases the bioavailability of lovastatin acid.
4. As the dose of Lovastatin XL increases from 10 to 40 mg, the plasma profiles (including the $AUC_{0-48hr}$ and $C_{max}$ values) of lovastatin appear to increase linearly.
5. Accumulation of lovastatin and its latent and active metabolites after chronic once-daily administration of Lovastatin XL is approximately 1.4- to 2-fold.
6. When compared to MEVACOR, the increased benefit on lipid levels produced by Lovastatin XL is achieved with similar systemic exposure to active (and total) inhibitors of HMC-CoA reductase. No evidence of unfavorable safety and tolerability characteristics is observed.

The foregoing description of a preferred embodiment of the invention has been presented for purposes of illustration and description. It is not intended to be exhaustive or to limit the invention precise form disclosed. In certain further preferred embodiments, the controlled release oral lovastatin formulations of the invention may be characterized by other pharmacokinetic values which are set forth in the data provided in the appended examples, which data can be readily gleaned by one of ordinary skill in the art reviewing the appended Tables and Figures. Such pharmacokinetic values may be derived in part based on parameters such as Cmax (ng/mL); Cmin (ng/mL); Tmax (hr); fluctuation (%)(expressed as the difference between Cmax and Cmin expressed as a percentage of Cmin); the area under the curve (AUC); and any combination thereof. Obvious modifications or variations are possible in light of the above 40 teachings. All such obvious modifications and variations are intended to be within the scope of the appended claims.

We claim:
1. A method for reducing serum cholesterol levels in humans comprising orally administering to a human on a once a day basis a controlled release lovastatin tablet comprising 10 to 80 mg of lovastatin and formulated with a core comprising the lovastatin and a water swellable polymer and a coating surrounding the core wherein the coating comprises a water insoluble polymer and a pH sensitive polymer that dissolves at a pH above 3 to release less than 20% of the lovastatin after 2 hours of in vitro testing and between 20% and 70% of the lovastatin after 5 hours of in vitro testing wherein the in vitro testing is conducted using a USP XXII, Type II dissolution apparatus in 2% sodium lauryl sulfate, pH 7.0 NaH$_2$PO$_4$ buffer at 37° C. and 50 rpms, so that a mean time to maximum plasma concentration of lovastatin after a single dose administration in the morning without food is at least about 12 hours and the ratio of $AUC_{0-48hr}$ of lovastatin for the controlled release dosage form to $AUC_{0-48hr}$ of lovastatin for an immediate release oral lovastatin tablet is greater than unity following the single dose administration of the controlled release tablet and immediate release tablet.

2. The method of claim 1 wherein pH sensitive polymer dissolves at a pH above 5.5.

3. The method of claim 1 wherein the controlled release tablet is an osmotic tablet.

4. A method for reducing serum cholesterol levels in humans comprising orally administering to a human on a once a day basis a controlled release lovastatin tablet comprising 10 to 80 mg of lovastatin and formulated with a core comprising the lovastatin and a water swellable polymer and a coating surrounding the core wherein the coating comprises a water insoluble polymer and a pH sensitive polymer that dissolves at a pH above 3, wherein: (a) the tablet releases 0 to about 25% of the lovastatin after 2 hours of in vitro testing, about 40 to about 85% of the lovastatin after 6 hours of in vitro testing and not less than about 75% of the lovastatin after 16 hours of in vitro testing wherein the in vitro testing is conducted using a USP XXII, Type II dissolution apparatus in 2% sodium lauryl sulfate, pH 7.0 NaH$_2$PO$_4$ buffer at 37° C. and 50 rpms; (b) a mean time to maximum plasma concentration of lovastatin of about 10 to about 32 hours is obtained after a single dose administration; (c) a mean time to maximum plasma concentration of lovastatin acid of about 13 to about 20.9 hours is obtained after a single dose administration; and (d) a ratio of $AUC_{0-48hr}$ of lovastatin for the controlled release tablet to $AUC_{0-48hr}$ of lovastatin for an immediate release oral lovastatin tablet is greater than unity and the ratio of $AUC_{0-48hr}$ of lovastatin acid for the controlled release tablet to $AUC_{0-48hr}$ of lovastatin acid for an immediate release oral lovastatin tablet is greater than unity following the single dose administration of the controlled release tablet and immediate release tablet.

5. The method of claim 4 wherein the controlled release tablet releases 0 to about 20% of the lovastatin after 2 hours of in vitro testing, about 50 to about 80% of the lovastatin after 6 hours of in vitro testing and not less than about 80% of the lovastatin after 16 hours of in vitro testing wherein the in vitro testing is conducted using a USP XXII, Type II dissolution apparatus in 2% sodium lauryl sulfate, pH 7.0 NaH$_2$PO$_4$ buffer at 37° C. and 50 rpms.

6. The method of claim 4 wherein the pH sensitive polymer dissolves at a pH above 5.5.

7. The method of claim 4 wherein the controlled release tablet is an osmotic tablet.

* * * * *